United States Patent
Schob et al.

(10) Patent No.: US 6,351,048 B1
(45) Date of Patent: Feb. 26, 2002

(54) ELECTRICAL ROTARY DRIVE

(75) Inventors: Reto Schob, Volketswil; Thomas Gempp, Zürich, both of (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 09/560,826

(22) Filed: Apr. 28, 2000

(30) Foreign Application Priority Data

Jun. 22, 1999 (EP) ............................................. 99810553
Dec. 3, 1999 (EP) ............................................. 99811115

(51) Int. Cl.[7] ................................................ H02K 7/09
(52) U.S. Cl. ..................... 310/90.5; 310/68 B; 318/721
(58) Field of Search ............................ 310/90.5, 68 B; 318/494, 495, 496, 721; 417/410.3

(56) References Cited

U.S. PATENT DOCUMENTS

| | | | |
|---|---|---|---|
| 4,392,693 A | * 7/1983 | Habermann et al. | 308/10 |
| 4,866,318 A | * 9/1989 | Habermann et al. | 310/90.5 |
| 5,491,622 A | 2/1996 | Carosa | 363/56 |
| 5,578,880 A | 11/1996 | Lyons | 310/90.5 |
| 5,627,421 A | * 5/1997 | Miller et al. | 310/90.5 |
| 5,729,066 A | * 3/1998 | Soung et al. | 310/90.5 |
| 5,754,425 A | * 5/1998 | Murakami | 310/90.5 |
| 6,005,315 A | * 12/1999 | Chapmann | 310/90.5 |
| 6,020,665 A | * 2/2000 | Maurio et al. | 310/90.5 |

FOREIGN PATENT DOCUMENTS

| | | | |
|---|---|---|---|
| EP | 0588628 A1 | 3/1994 | B60L/11/18 |
| GB | 2276050 A | 9/1994 | H02P/6/02 |
| WO | WO 96/31934 | 10/1996 | H02K/7/09 |
| WO | WO 98/11650 | 3/1998 | H02K/7/09 |

OTHER PUBLICATIONS

Patent Abstracts of Japan; vol. 18, No. 681 (E–1649), Dec. 21, 1994 & JP 06 269144 A (Shinko Electric Co. Ltd), Sep. 22, 1994 Abstract.
Patent Abstracts of Japan; vol. 18, No. 434 (E–1592), Aug. 12, 1994 & JP 06 133493 A (Shinko Electric Co. Ltd), May 13, 1994 Abstract.
Patent Abstracts of Japan; vol. 96, No. 7 Jul. 31, 1996 & JP 08 084491 A (Ebara Corp), Mar. 26, 1996 Abstract.
Patent Abstracts of Japan; vol. 17, No. 3 (E–1301), Jan. 6, 1993 & JP 04 236188 A (Toshiba Corp), Aug. 25, 1992 Abstract.

* cited by examiner

*Primary Examiner*—Burton S. Mullins
(74) *Attorney, Agent, or Firm*—Townsend and Townsend and Crew LLP

(57) ABSTRACT

An electrical rotary drive, designed as a bearingless motor, has a magnetically journalled rotor (3) and a stator (2) which comprises a drive winding (6) having at least two loops (61, 62) for producing a magnetic drive field which produces a torque on the rotor (3), and has a control winding (7) having at least three loops (71, 72, 73, 74) for producing a magnetic control field by means of which the position of the rotor (3) with respect to the stator (2) can be regulated, with each loop (61, 62) of the drive winding (6) belonging to a different electrical drive phase and each loop (71–74) of the control winding (7) belonging to a different electrical control phase, and having a setting device (4) which supplies each loop (61, 62) of the drive winding (6) and each loop (71–74) of the control winding (7) with a phase current or a phase voltage as a setting parameter, with the setting device (4) being designed in such a manner that the setting parameter for each loop (61, 62) of the drive winding (6) and for each loop (71–74) of the control winding (7) can be regulated independently of the setting parameters for the other loops.

21 Claims, 19 Drawing Sheets

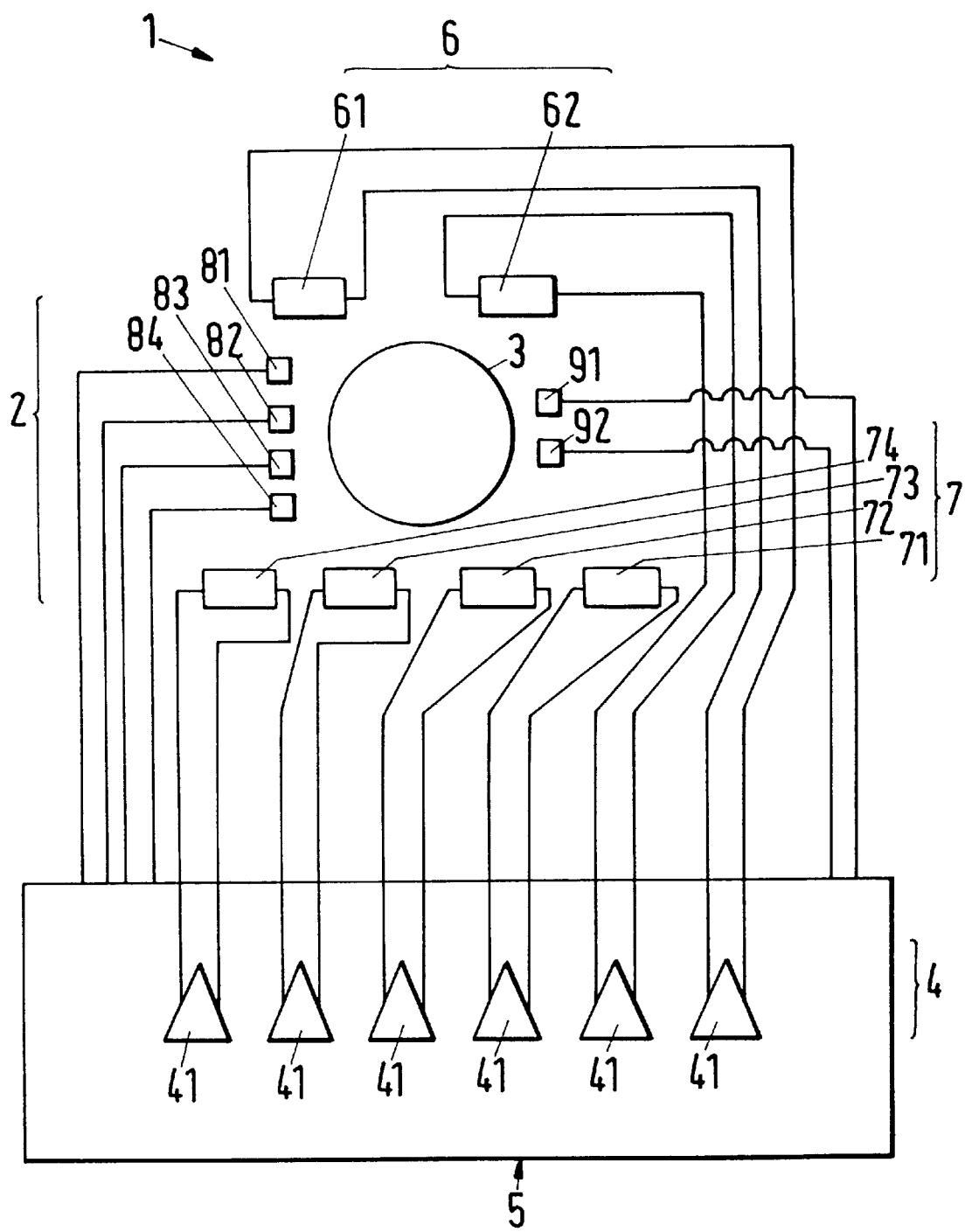

Figure 6:
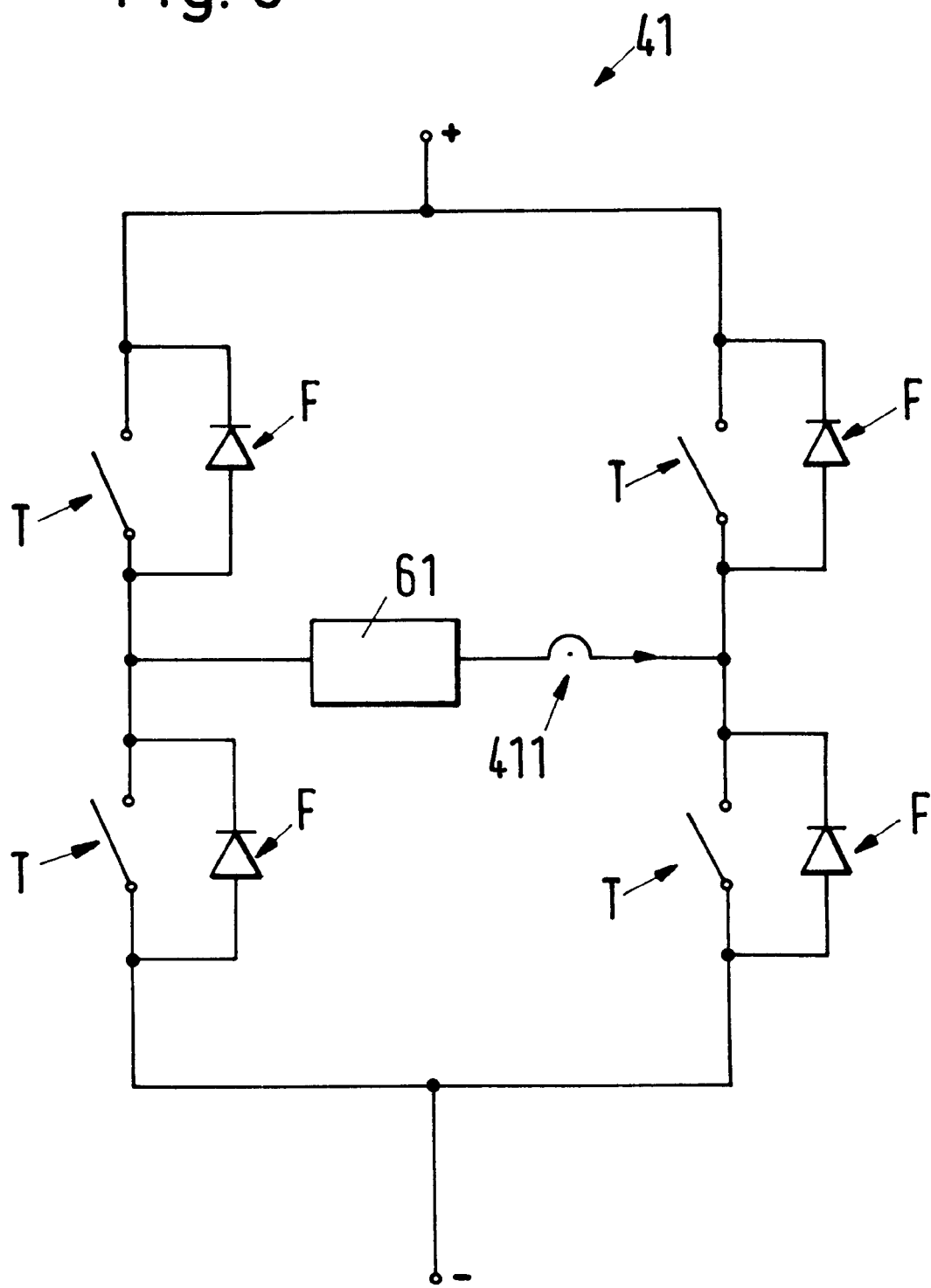

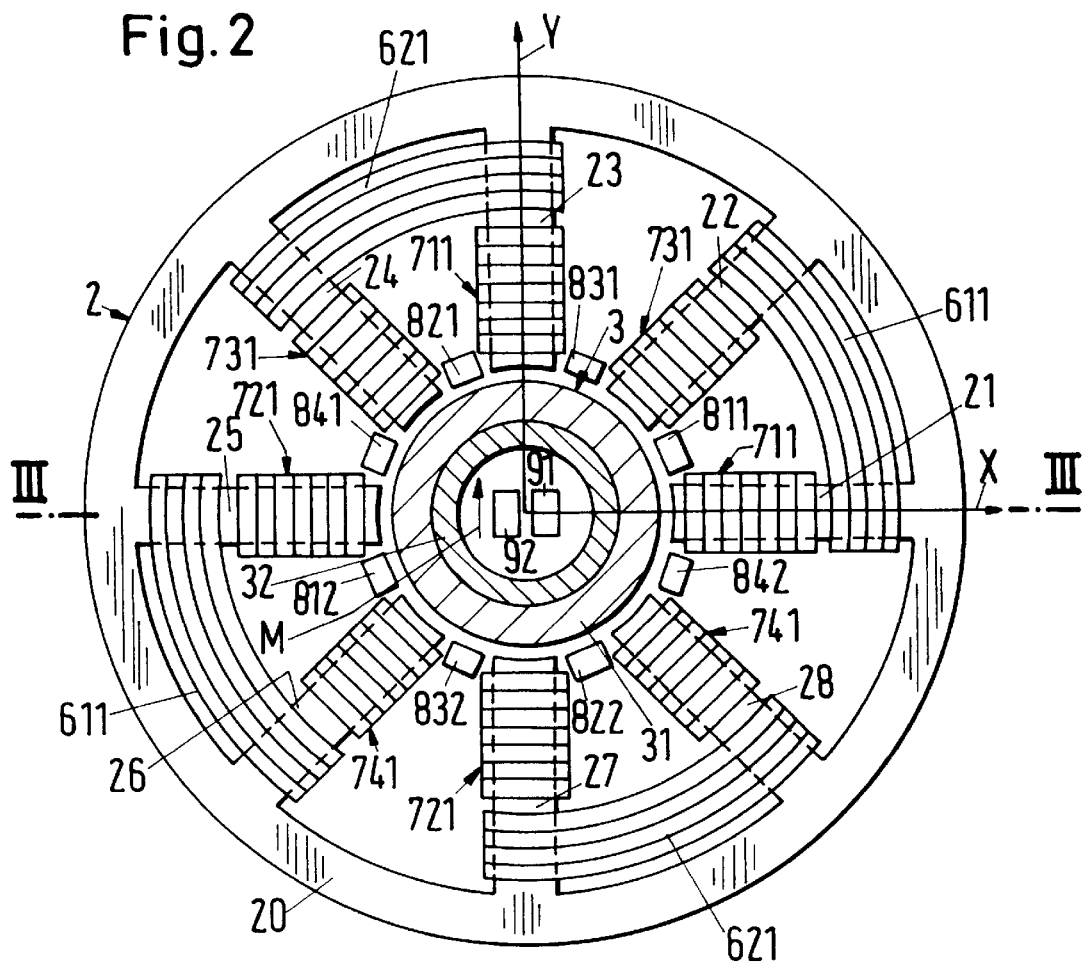
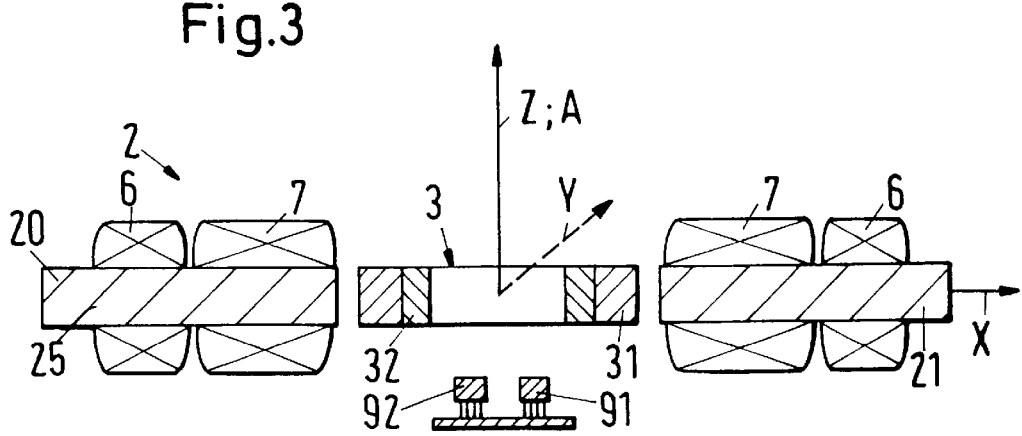

Fig.4
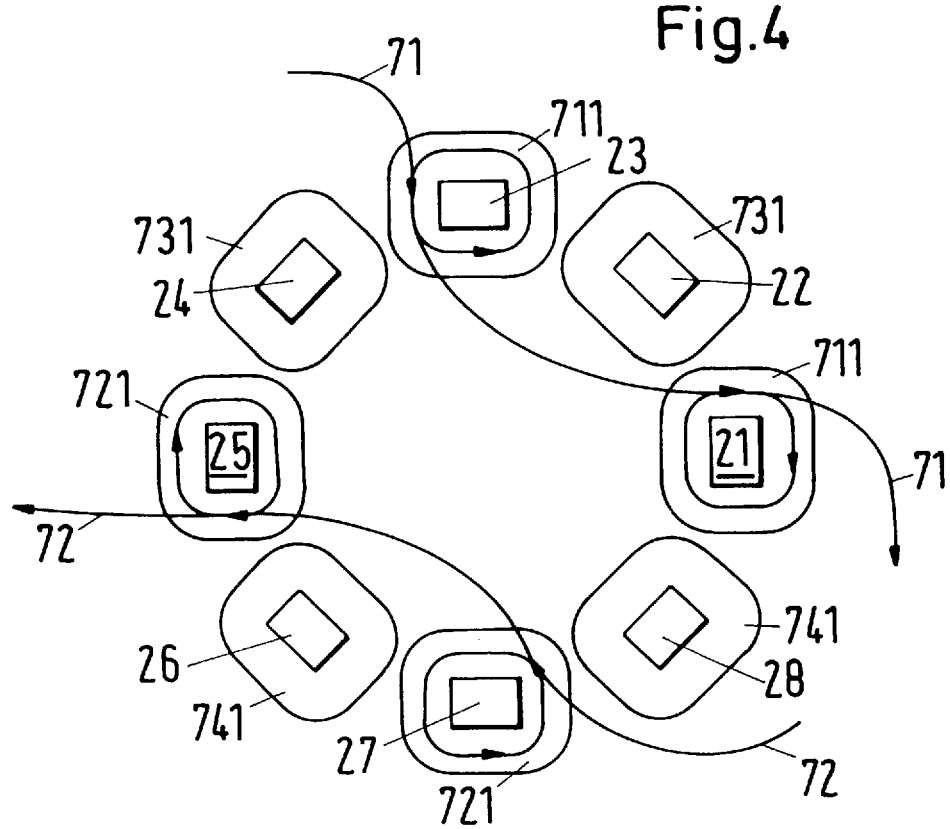
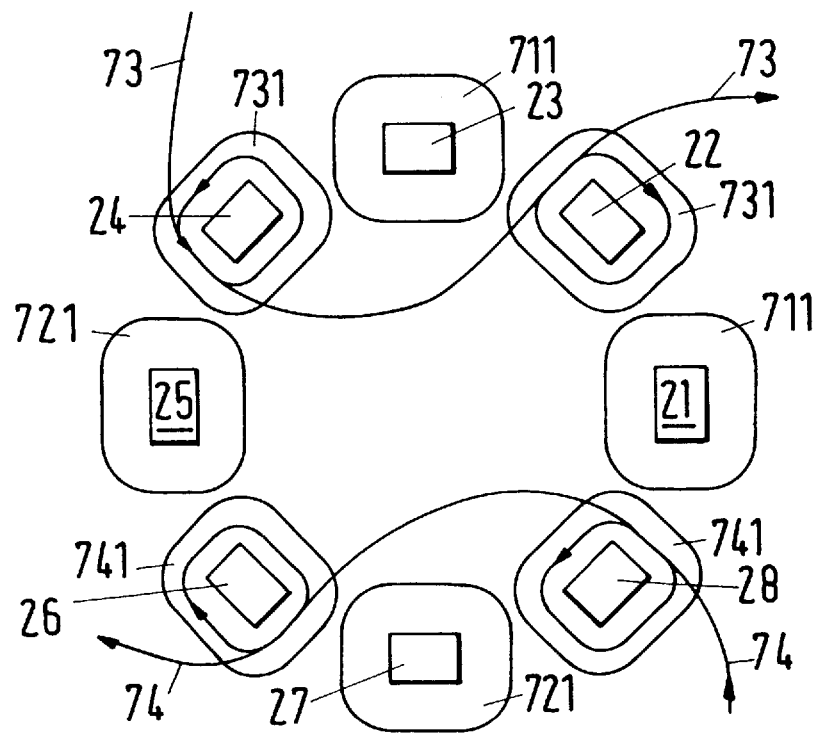

Fig. 5
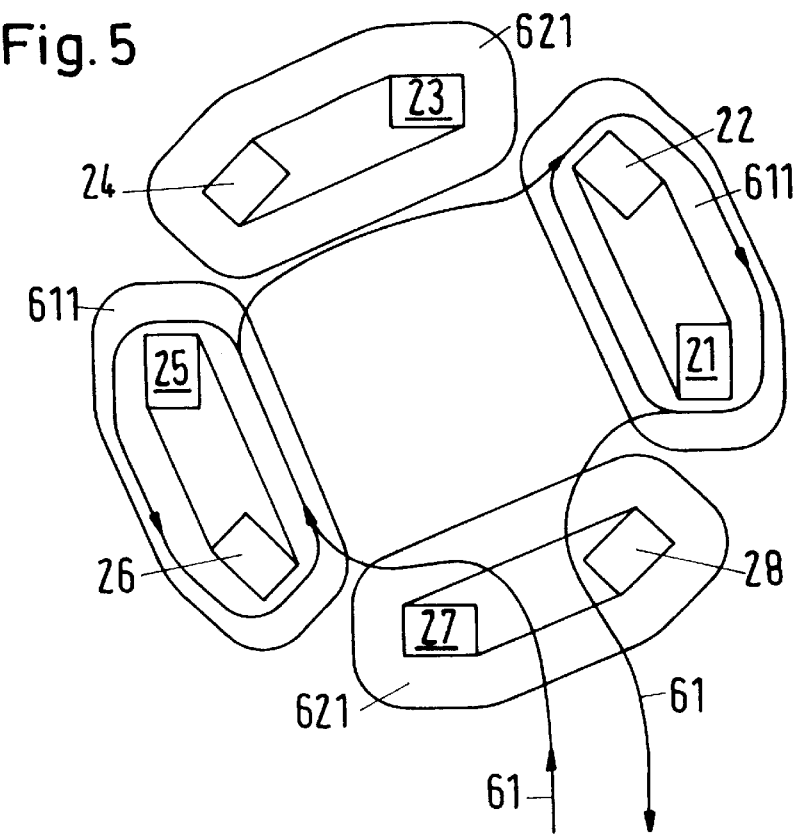
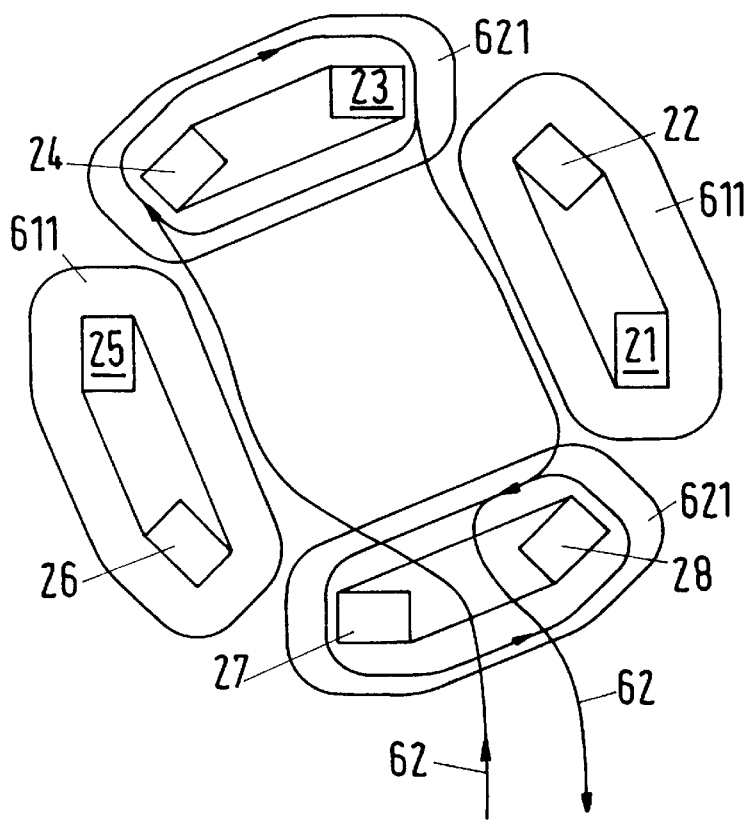

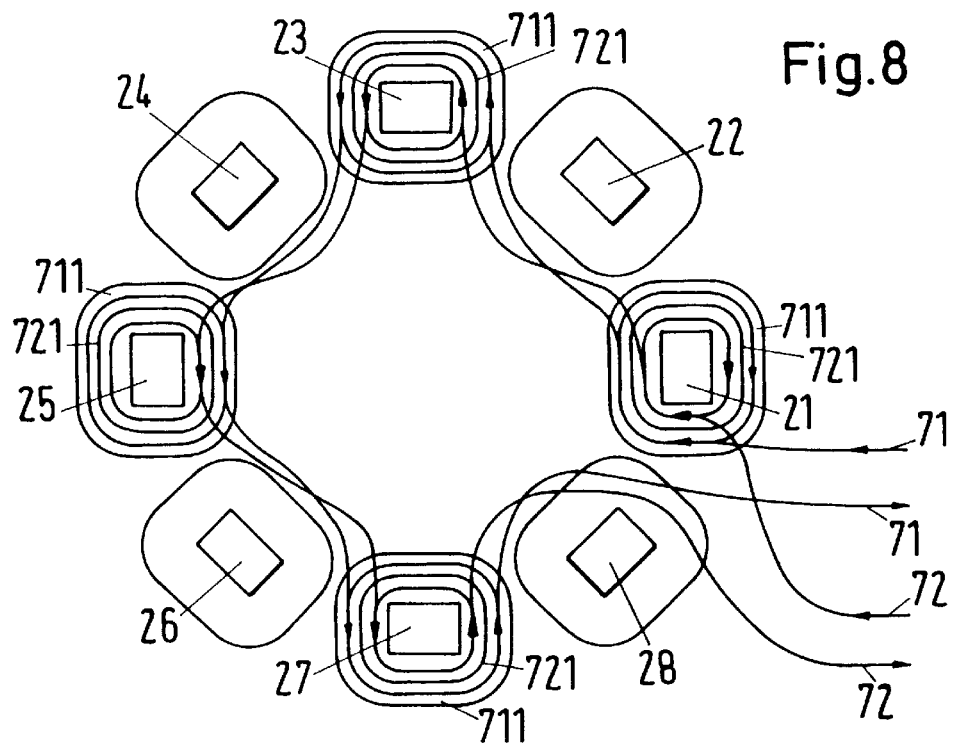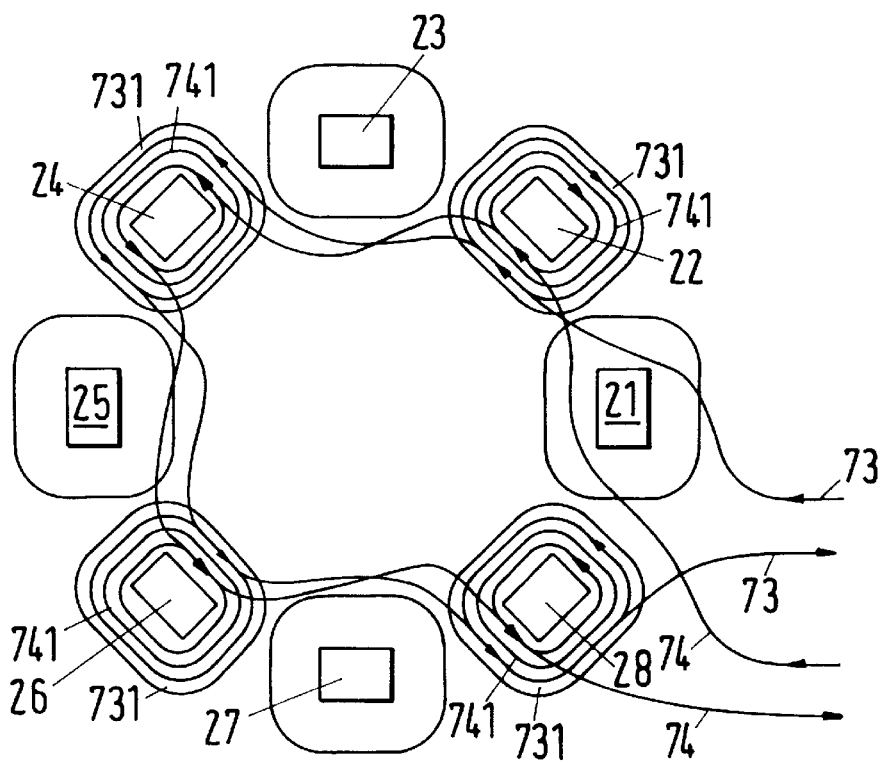
Fig.8

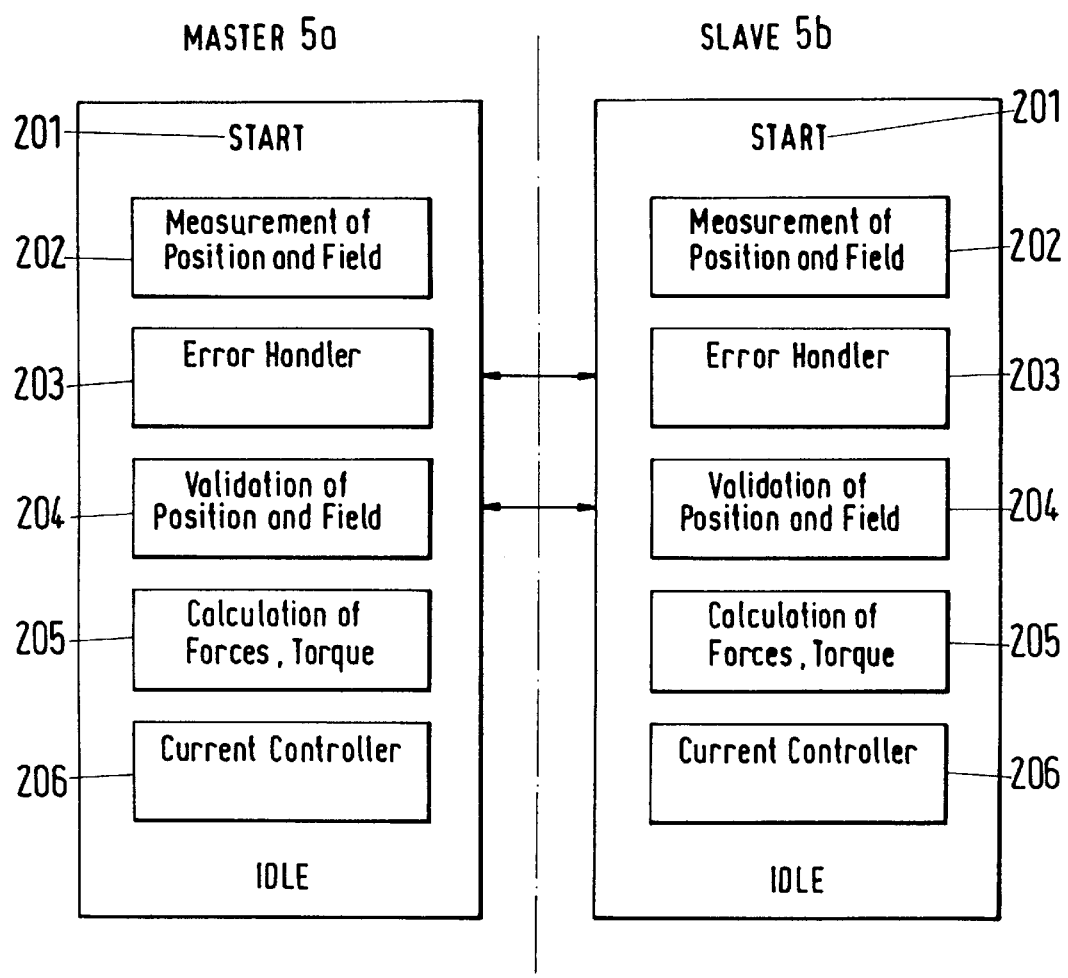

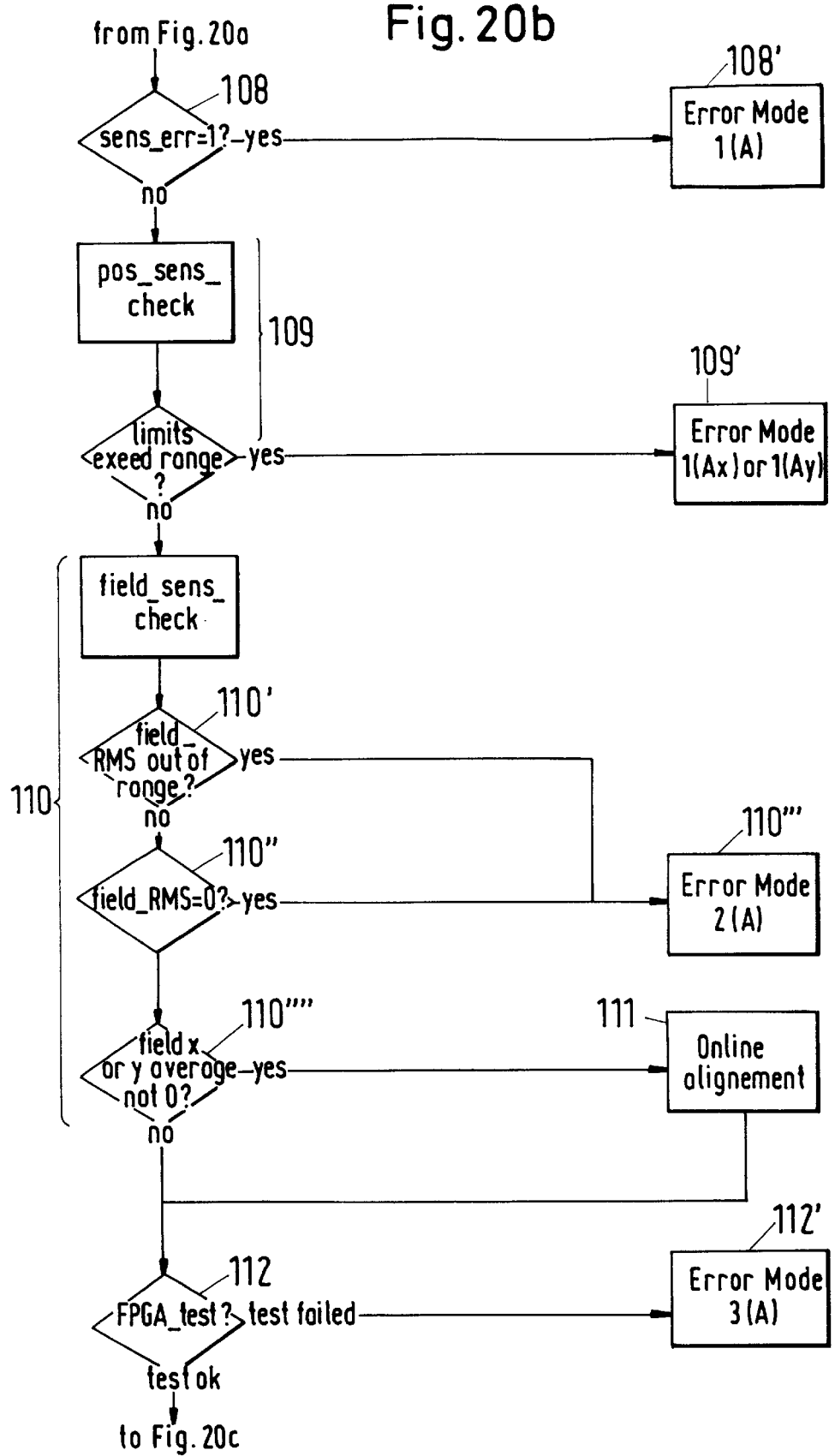

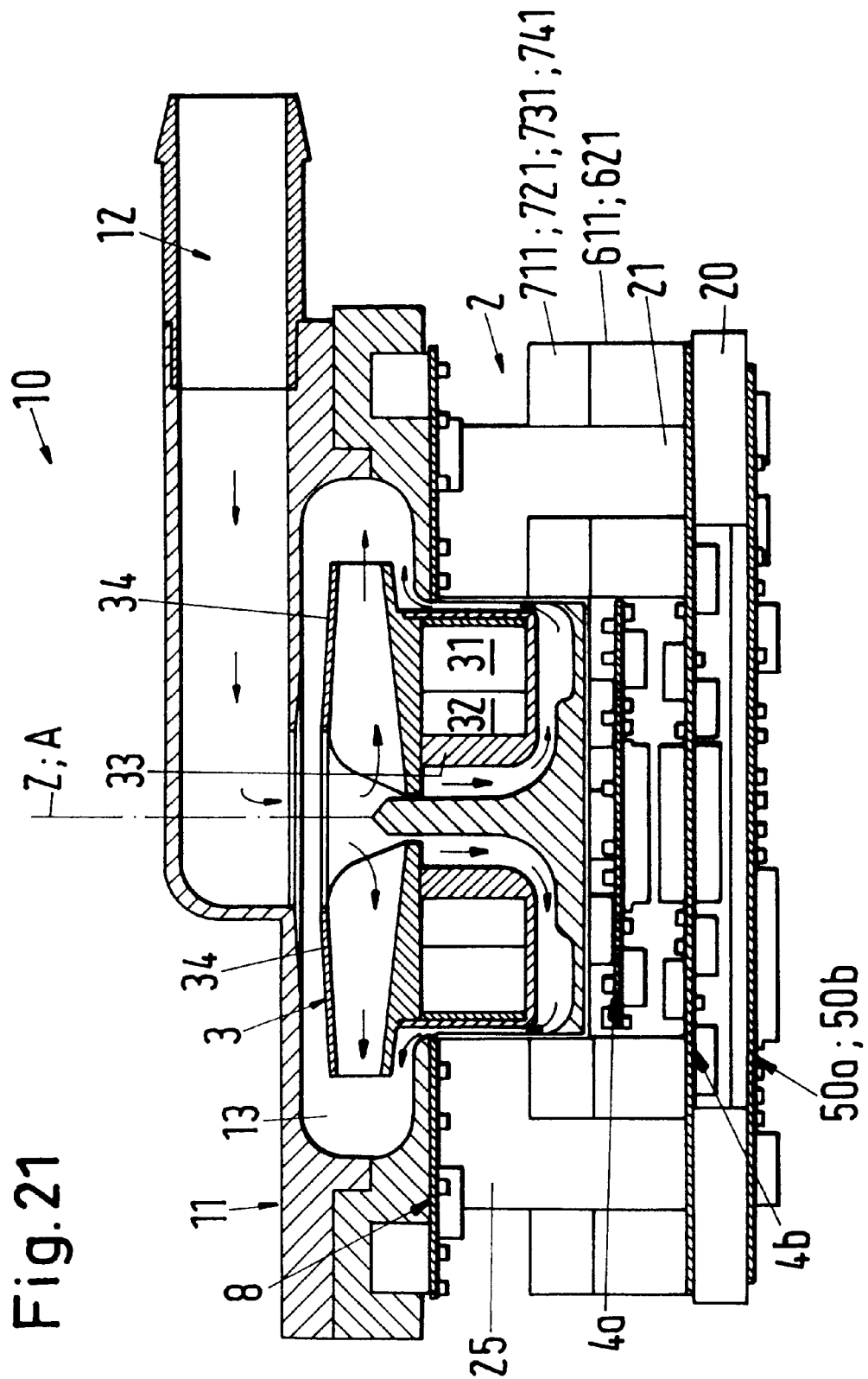

ELECTRICAL ROTARY DRIVE

The invention relates to an electrical rotary drive in accordance with the preamble of independent claim 1, and to a blood pump with a rotary drive of this kind.

Blood pumps, which are usually designed as axial or as centrifugal pumps, serve for the forwarding of blood and are used for example in the framework of operations on the heart for maintaining the blood circulation. Furthermore, implantable blood pumps are known which are implanted into the body of the patient for the temporary or chronic support of the heart activity.

In blood pumps it must be ensured that no contamination of the forwarded blood occurs. Therefore in blood pumps the rotor of the electromagnetic drive and/or the pump rotor is/are preferably magnetically journalled without contact. This magnetic journalling of the rotor can be realized either through separate magnetic bearings, that is, bearings which are different from the drive; or the magnetic journalling is realized by the stator of the drive.

In WO-A-96/31934 for example a rotation pump is disclosed which is suitable as a blood pump and which is designed as a so-called bearingless motor. This is an electromagnetic rotary drive in which the rotor is journalled without contact with respect to the stator by means of magnetic forces, with no separate magnetic bearings being present for the rotor. For this the stator is designed as a bearing and drive stator comprising a drive winding and a control winding. With these two windings a magnetic rotary field can be produced which on the one hand exerts a torque on the rotor which causes it to rotate, and which on the other hand exerts any desired settable transverse force on the rotor, so that its radial position can be actively controlled or regulated respectively. Thus three degrees of freedom of the rotor can be actively regulated. With respect to three further degrees of freedom, namely its axial deflection in the direction of the axis of rotation and tiltings with respect to the plane which is perpendicular to the axis of rotation (two degrees of freedom) the rotor is passively magnetically, which means not controllably, stabilized through reluctance forces.

The term "bearingless motor" is to be understood in this sense for the following explanations. With respect to the further details of the design and especially of the control or regulation respectively of the bearingless motor, reference is made here, in addition to the already cited WO-A-96/31934, to WO-95/18925.

Furthermore, blood pumps should be compact and space saving, in particular in the case of an implantation in the body, but nevertheless be able to achieve a pumping performance which corresponds at least to that of the heart. For this it is proposed e.g. in WO-A-96/31934 to provide the rotor of the bearingless motor with vanes, so that the rotor of the rotary drive is identical to the pump rotor, and thus forms an integral rotor. This rotor thus serves as a drive rotor, a bearing rotor and a pump rotor, through which a very compact and high performance blood pump can be realized.

A problem in known bearingless motors is to be seen in that when faults arise, such as for example the failure of an amplifier stage or the breaking of an electrical line in one of the phases of the stator, a correct functioning of the drive and/or of the magnetic journalling of the rotor is no longer ensured. This represents an enormous safety hazard in particular in very sensitive uses, e.g. in implanted blood pumps. A failure of the rotor drive or of the magnetic rotor journalling can namely have very severe, possibly even fatal consequences. The invention is thus dedicated to the task of significantly reducing this safety hazard.

The object of the invention is therefore to provide an electrical rotary drive which is designed as a bearingless motor and which is fault tolerant both with respect to the magnetic journalling of the rotor and with respect to the driving of the rotor, which means that a correct operation of the bearingless motor with reliable magnetic journalling of the rotor and reliable driving of the rotor should still be possible when faults arise.

The electrical rotary drive which satisfies this object is characterized by the features of the independent claim 1.

The electrical rotary drive in accordance with the invention, designed as a bearingless motor, thus has a magnetically journalled rotor and a stator which comprises a drive winding having at least two loops for producing a magnetic drive field which produces a torque on the rotor, and a control winding having at least three loops for producing a magnetic control field by means of which the position of the rotor with respect to the stator can be regulated, with each loop of the drive winding belonging to a different electrical drive phase, and with each loop of the control winding belonging to a different electrical control phase, as well as a setting device which provides each loop of the drive winding and each loop of the control winding with a phase current or a phase voltage as a setting parameter, with the setting device being designed in such a manner that the setting parameter for each loop of the drive winding and for each loop of the control winding can be regulated independently of the setting parameters for the other loops.

For this the setting device preferably comprises for each loop of the drive winding and for each loop of the control winding a separate bipolar power amplifier, which is integrated into a control apparatus for the rotary drive.

The rotary drive in accordance with the invention, which is designed as a bearingless motor, operates in fault-free normal operation with at least two drive phases and at least three control phases. The terms "drive phase" and "control phase" respectively are used in each case to mean a loop of the drive winding or of the control winding respectively and the part of the setting device which supplies it. Since the setting parameters, that is, the phase voltage or the phase current, can be regulated for each loop of the drive winding and for each loop of the control winding completely independently of the setting parameters for the other loops, each drive phase and each control phase can be operated independently of the remaining electrical phases. Thus the rotary drive can continue to be operated with a reduced number of drive phases and/or control phases respectively when a fault arises in a drive phase and/or a control phase, e.g. in the event of a failure of a complete phase, without concessions regarding the correct functioning either of the magnetic journalling or of the driving of the rotor of the rotary drive being necessary.

The minimum requirement for an enduring correct operation is that one drive phase and two control phases of the rotary drive are still fault-free, which means that at least one drive phase and at least one control phase can fail completely without the reliable operation of the rotary drive being endangered. Depending on how many drive and control phases the rotary drive in accordance with the invention is equipped with, it can still continue to be operated even after a failure of a plurality of drive and/or control phases.

Since the rotary drive in accordance with the invention can be operated with a reduced number of phases, it is in principle irrelevant where a fault arises in a drive phase or in a control phase. Thus for example a power amplifier can fail, or a break can occur in a line in one loop of the drive winding or of the control winding respectively, or a short circuit can arise in a power amplifier or in a winding loop of the drive or the control winding; and in spite of such a fault a further reliable operation of the rotary drive is possible. As a result of this high fault tolerance the rotary drive in accordance with the invention brings about a considerable increase in the operating reliability.

The rotary drive in accordance with the invention with its at least two-phase design of the drive winding in the fault-free normal case is preferably a permanent-magnetically excited rotary field motor, thus in particular a permanent-magnetically excited synchronous motor or a brush-less d. c. motor (in spite of its generally usual name, the latter is essentially a rotary field motor). This means that the drive field which is produced by the stator is a rotary magnetic field, which drives the permanent-magnetic rotor. In the event that only one fault-free phase is available any longer for the operation due to a fault in one or more drive phases, then the rotary field motor becomes a single-phase a. c. motor.

The design of the bearingless motor as a permanent-magnetically excited rotary drive, that is, with a permanent-magnetically excited rotor, has the advantage in contrast with field-excited rotary drives that no current and thus no energy is required for the field excitation. The permanent-magnetic excitation thus enables a very economical operation with a comparatively low energy consumption This is a substantial advantage in particular for blood pumps and especially for implantable blood pumps, since in general an arbitrarily large energy supply is not available for the latter.

As is usual for the bearingless motor (see z. B. WO-A-98/11650) those designs of the rotary drive in accordance with the invention are preferred in which the drive winding has a number of pole pairs equal to p and the control winding a number of pole pairs equal to p+1 or p−1, which means that the numbers of pole pairs of the windings differ by one.

In accordance with a preferred exemplary embodiment the rotary drive has exactly three drive phases and exactly three control phases. In a design of this kind the rotary drive can still reliably drive and journal the rotor even in the event of the complete failure of two drive phases and one control phase.

In particular in regard to a design which is as compact, simple and space saving as possible, those embodiments are furthermore preferred in which exactly two drive phases and exactly four control phases are provided. Through this measure it is possible to reduce the number of stator teeth and the number of coils for the drive and the control winding, through which the cost and complexity of the apparatus, the complexity and size of the bearingless motor can be reduced. At the same time the fault tolerance with respect to the failure of one drive phase and the failure of at least one control phase is preserved. In embodiments of this kind the stator preferably has exactly eight stator teeth, between which the rotor is journalled. This has the additional advantage that there is more room in the grooves between the stator teeth, for example for sensor elements of the position sensors.

In accordance with a preferred embodiment the control winding comprises a plurality of concentrated control coils, each of which is wound around a different stator tooth.

In regard to a fault tolerance of the bearingless motor in accordance with the invention which is as great as possible, two separate control systems are preferably provided, each of which comprises the following components:

at least two position sensors for measuring the radial position of the rotor in the stator, means for determining the rotor angle, for example field sensors, at least three power amplifiers for supplying the individual loops of the drive and the control winding, a signal processing and regulation device for the regulation of the drive and the position of the rotor and for controlling the power amplifiers, with each control system controlling at least one drive phase and at least two control phases.

Through this measure the bearingless motor is operated by two nearly identical control systems, which can operate independently of one another. Since each control system comprises the components which are necessary for the operation of the bearingless motor, such as e.g. position sensors, means for determining of the rotor angle and regulation devices and power amplifiers for at least one drive phase and at least two control phases, each control system can take over the control and the regulation of the bearingless motor alone and immediately. In fault-free normal operation both control systems control the bearingless motor in common. In the event of a fault, however, the reliable operation can immediately be ensured with one of the two control systems. This so-called hot redundancy brings about yet a further considerable increase in the fault tolerance and thus in the operating reliability.

Furthermore, communication means are preferably provided for the communication between the two control systems. From this a further increase in the operating reliability results in particular in normal operation, in which both control systems are active. Since for example each control system has its own position sensors, the measurement of the position of the rotor is overdetermined in normal operation. In that the control systems have communication means which exchange the values for the position of the rotor which they in each case measure, this redundancy can advantageously be used for checking the position sensors. Analogous remarks hold for the field sensors and the rotor angle respectively.

Furthermore, fault detection means are preferably provided, by means of which faults in the control systems and/or in the individual drive phases and/or in the individual control phases and/or in the energy supply can be detected. These fault detection means can be designed as components both of the hardware and of the software. In accordance with a further advantageous measure the fault detection means can, in the event of the detection of a fault, eliminate the latter or switch over the rotary drive into a suitable one of a plurality of possible fault modes depending on the nature of the fault. In these fault modes parts of a control system or else an entire control system, or individual loops of the drive or control winding can be deactivated. Since more than one fault mode is provided, the control systems can react very flexibly and in a manner which is adapted to the respectively arising fault and take only the respectively necessary components out of operation, or no longer use them respectively.

In particular in regard to blood pumps it should be possible to design the bearingless motor in accordance with the invention very compactly and space savingly. In this regard it is advantageous to design each control system at least partly in the form of electronic prints which are arranged in the interior of the rotary drive.

In this the electronic prints which are arranged in the interior of the rotary drive are all power amplifiers and are arranged in such a manner that the individual power amplifiers are in each case connected directly to the associated drive and control coils respectively, that is, without cables. Through this measure the number of cable wires which lead away to the outside from the bearingless motor can be reduced to a minimum. Since experience shows cable connections to have the highest dropout rate of all components, a further increase in the reliability results from this.

The arranging of the electronic prints in the interior of the rotary drive is possible without problem in particular in combination with a preferred design of the rotary drive as a so-called temple motor. In a temple motor, such as is for example disclosed in WO-A-98/11650 (See FIG. 8 there and the associated text passages), the stator has a plurality of stator teeth which are connected by a yoke and which are in each case formed in L shape, with the longer limb extending in the axial direction, which is determined by the desired axis of rotation of the rotor, and with the shorter limb extending radially inwardly. Here the electronic prints can be arranged in the space which is surrounded by the longer limbs of the stator teeth.

A further advantageous measure consists in providing an evaluation module for the position sensors in a temple motor which is designed as an electronic print and which is arranged on the shorter limbs of the stator teeth in such a manner that the components which are provided on the electronic print are located in the free space between the stator teeth. An ideal utilization of the space in the bearingless motor results from this.

It is also advantageous to connect individual electronic prints to one another through flexible connection prints (flexprints). The substantially rigid electronic prints and the flexprints thus form namely a compound, a so-called rigid flex compound, which can be manufactured, equipped and tested as a unit.

Furthermore, a blood pump with an electrical rotary drive in accordance with the invention is proposed by the invention, with the rotor of the rotary drive being permanent-magnetically excited and having a plurality of vanes for forwarding the blood, so that the rotor of the rotary drive also serves as pump rotor. A blood pump of this kind is fault tolerant to a high degree, extremely reliable, compact, of high performance and economical in regard to the energy requirement. It is suitable for uses inside and outside the body.

Further advantageous measures and preferred designs of the invention result from the subordinate claims.

Figure 7:
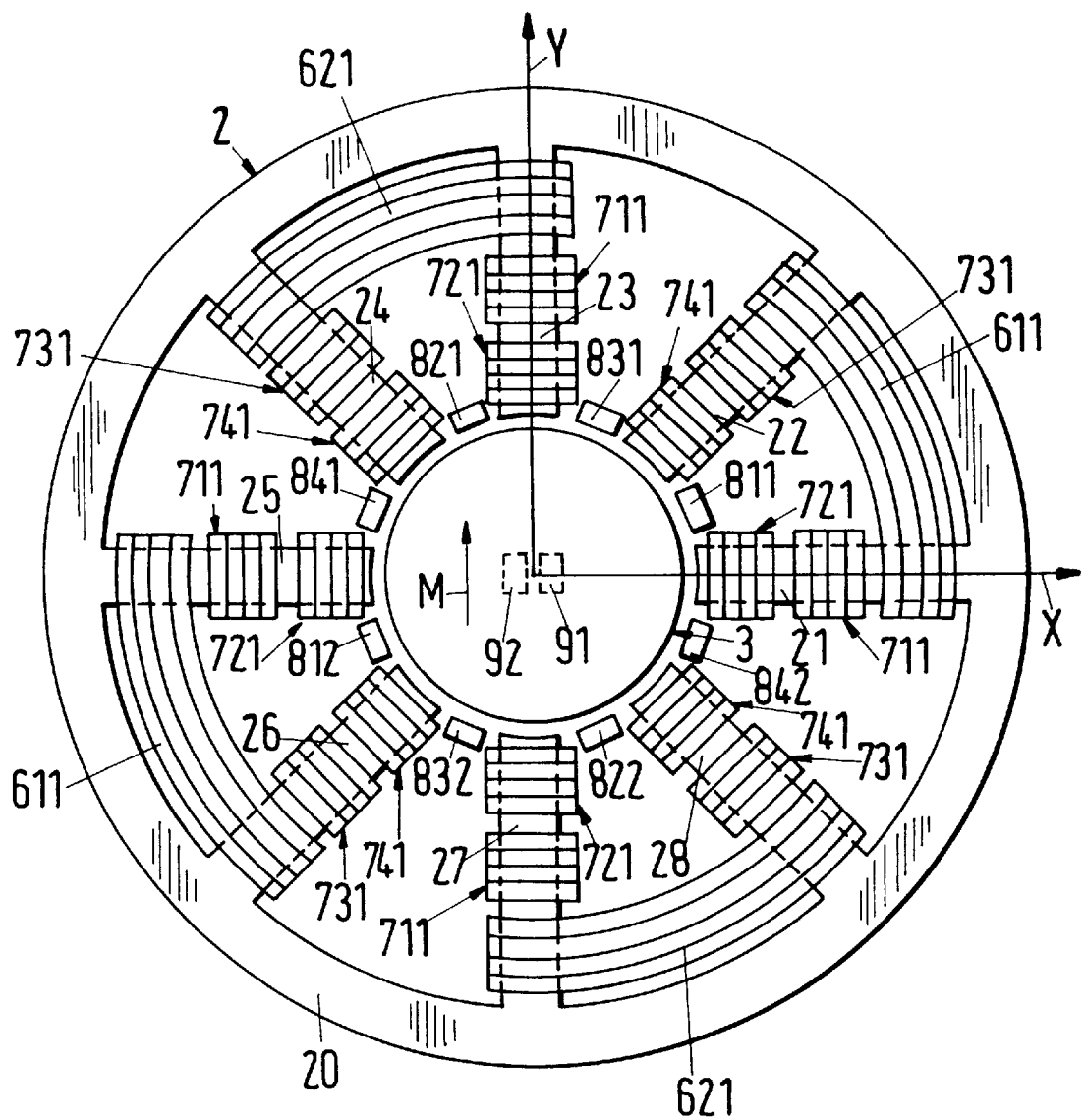
Figure 9:
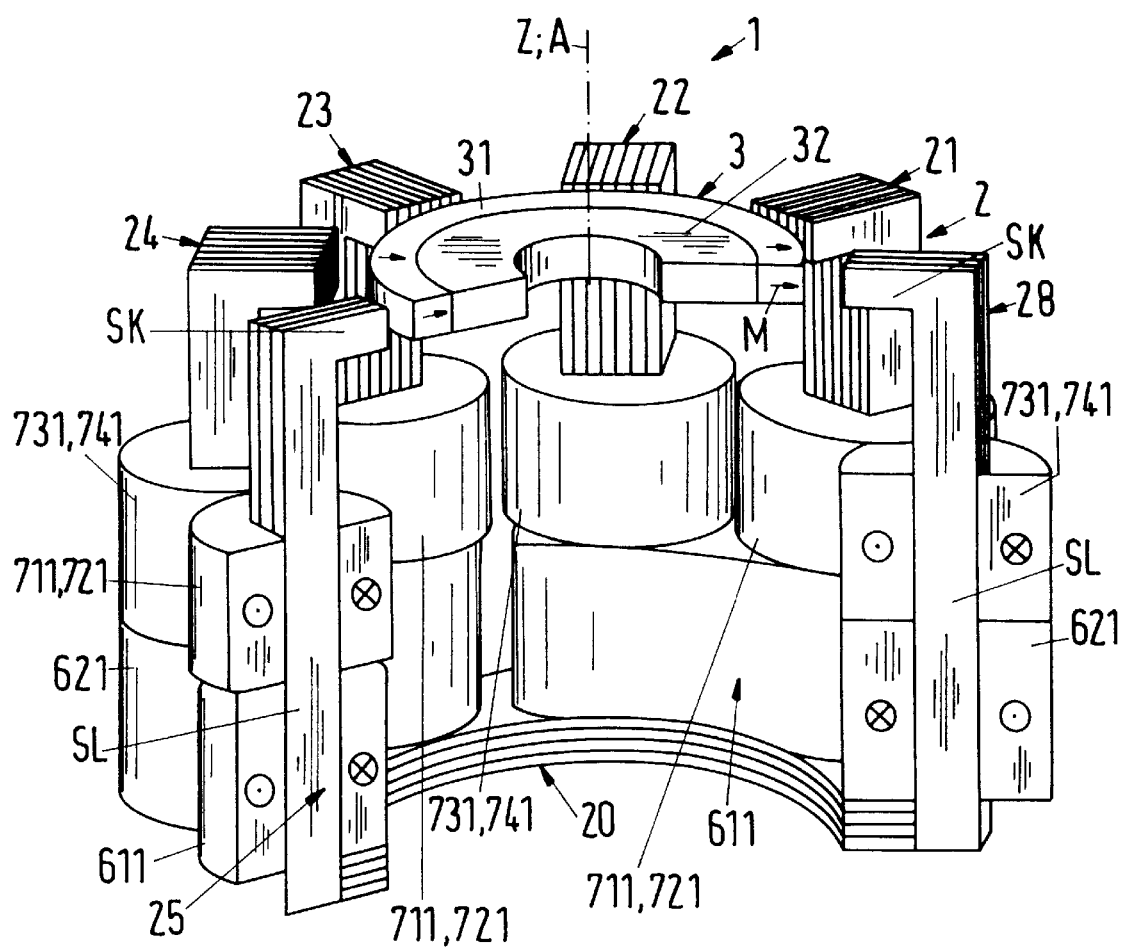
Figure 10:
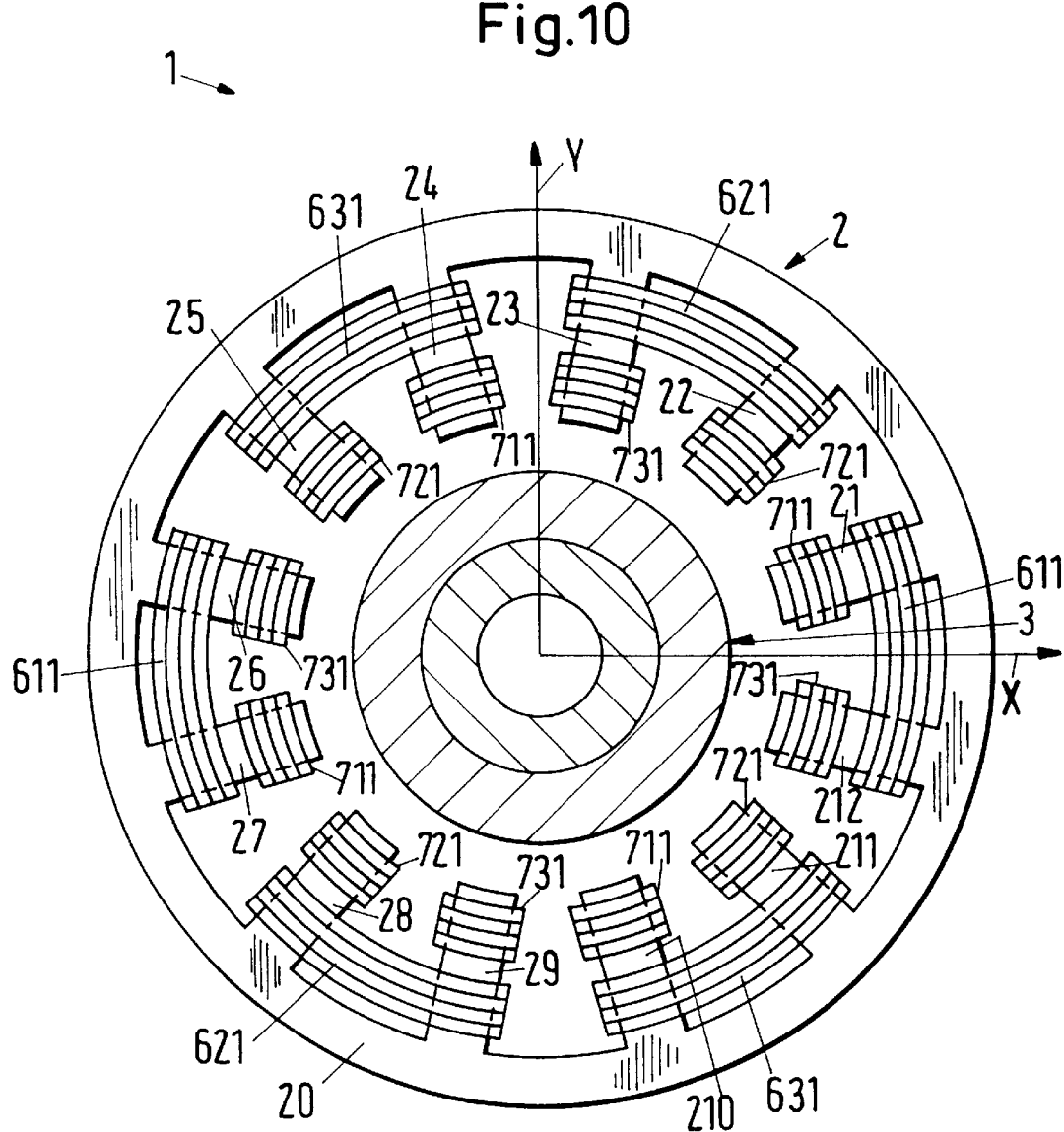
Figure 11:
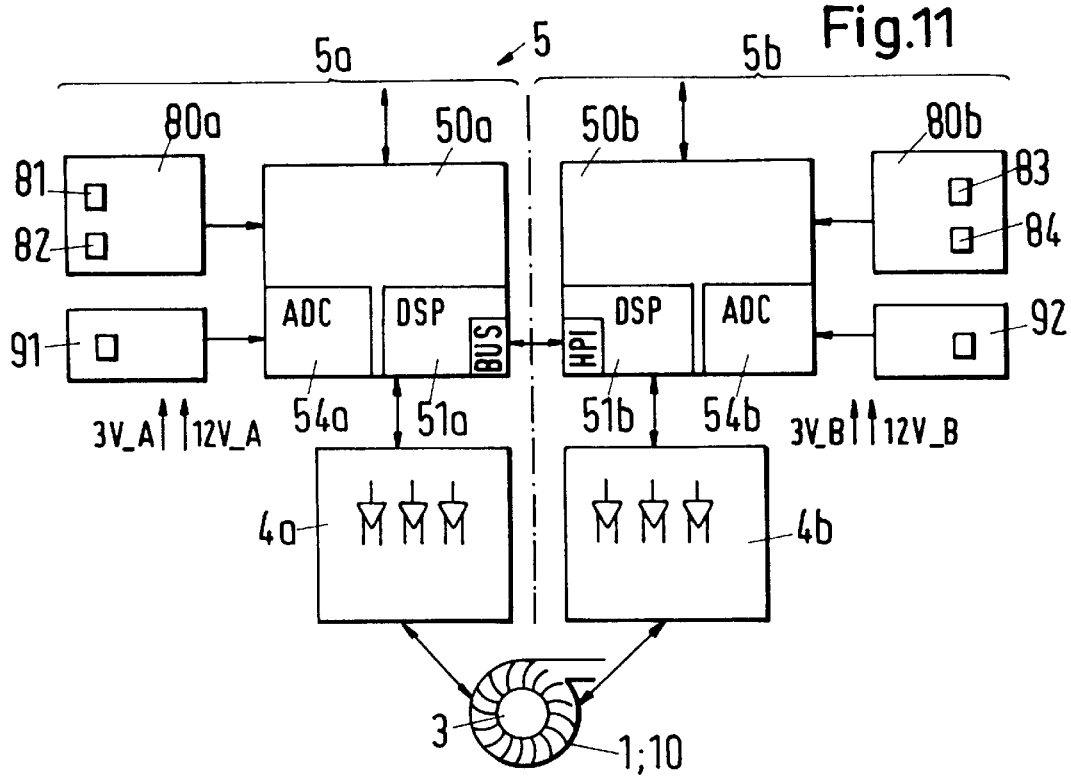
Figure 12:
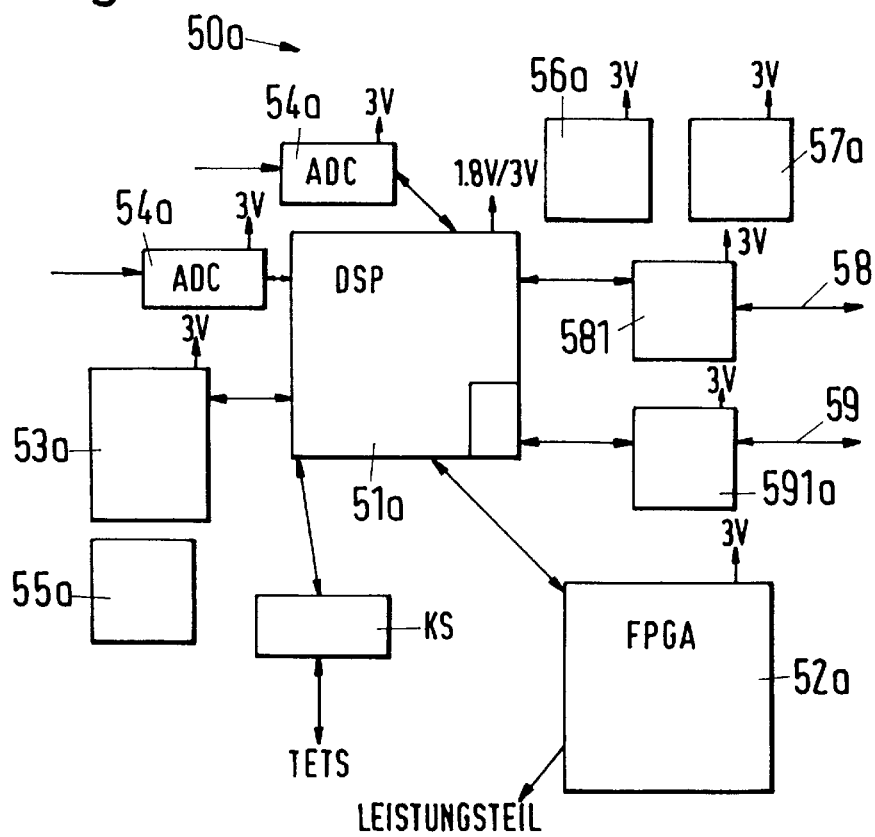
Figure 13:
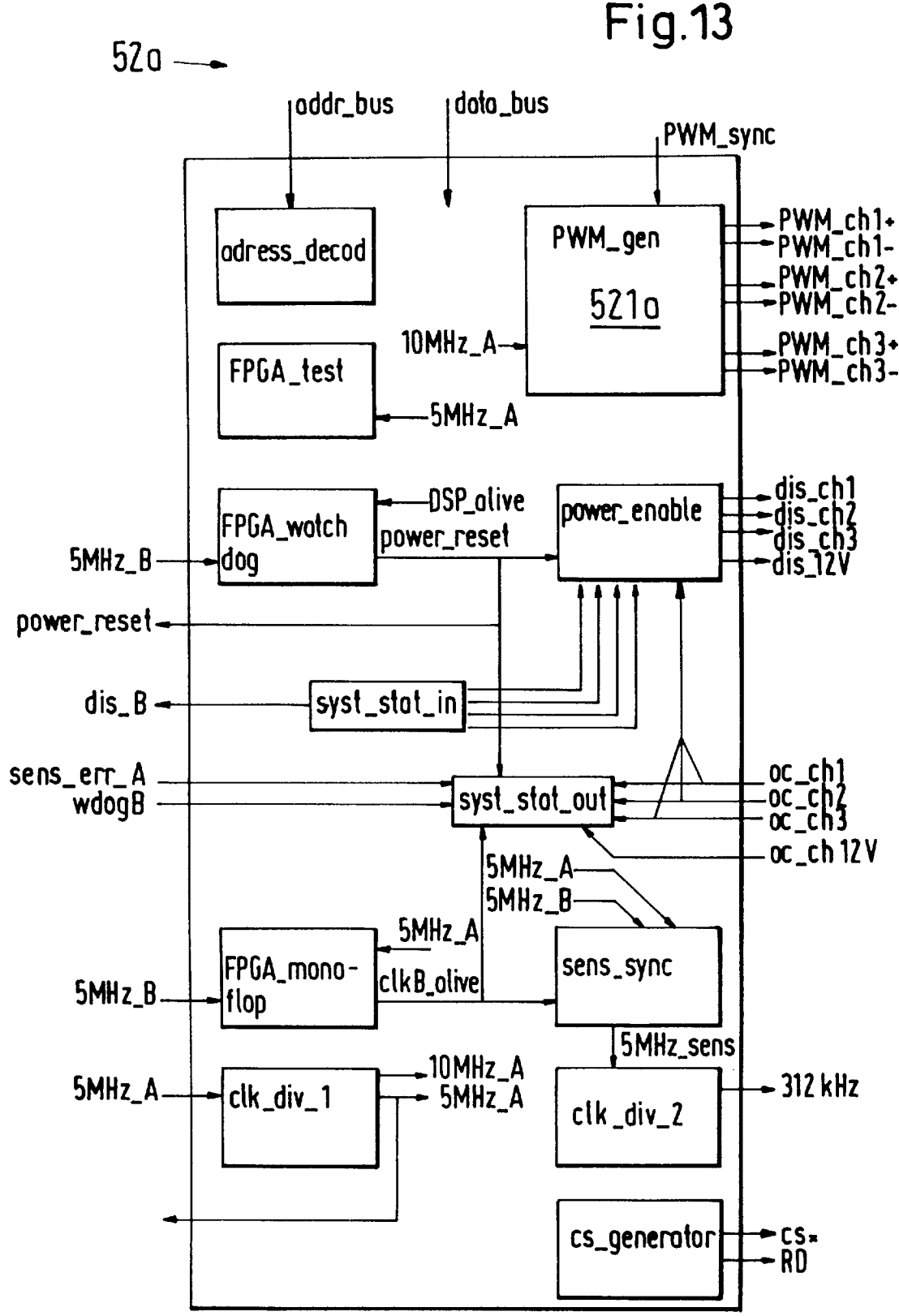
Figure 14:
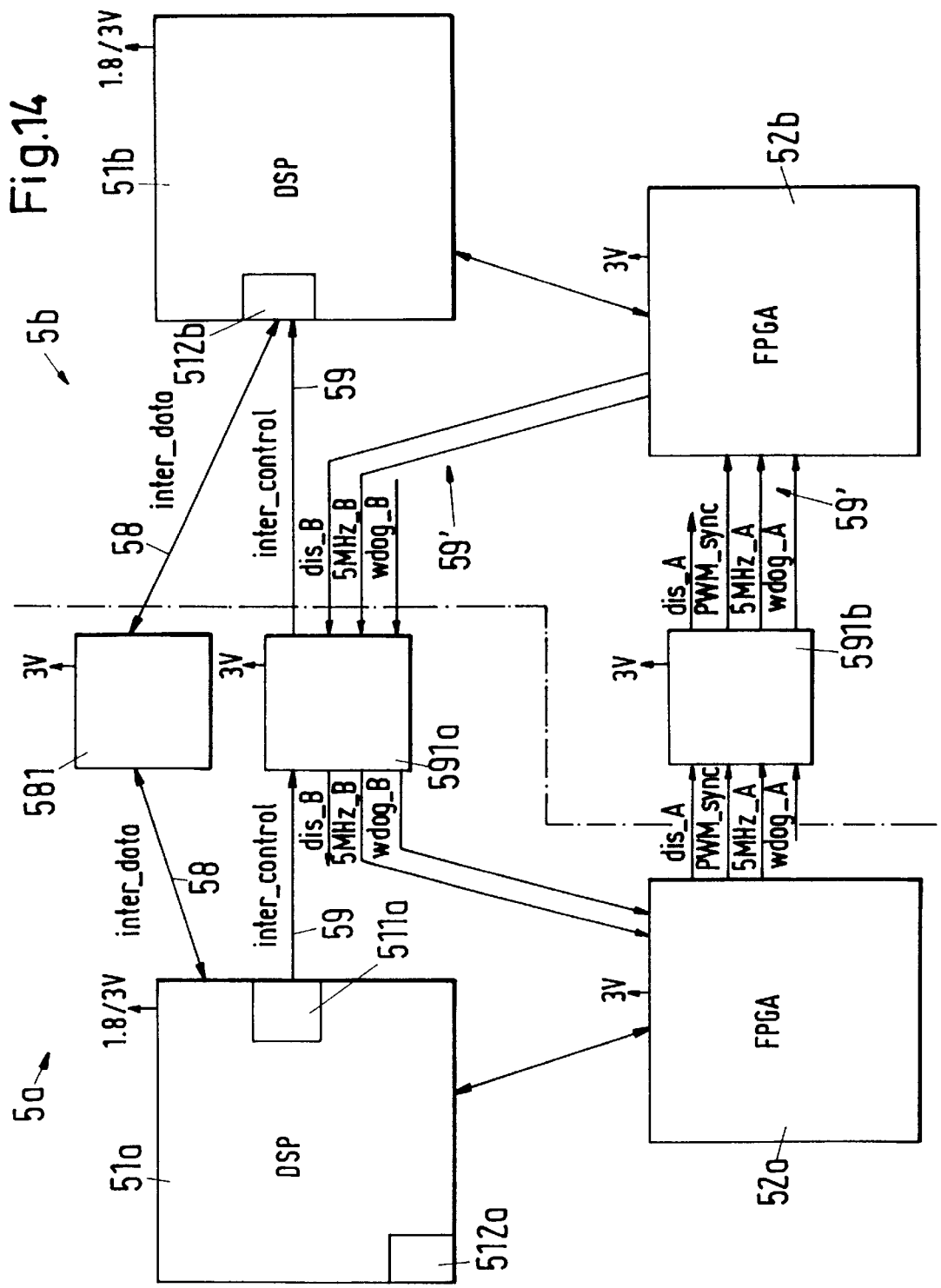
Figure 15:
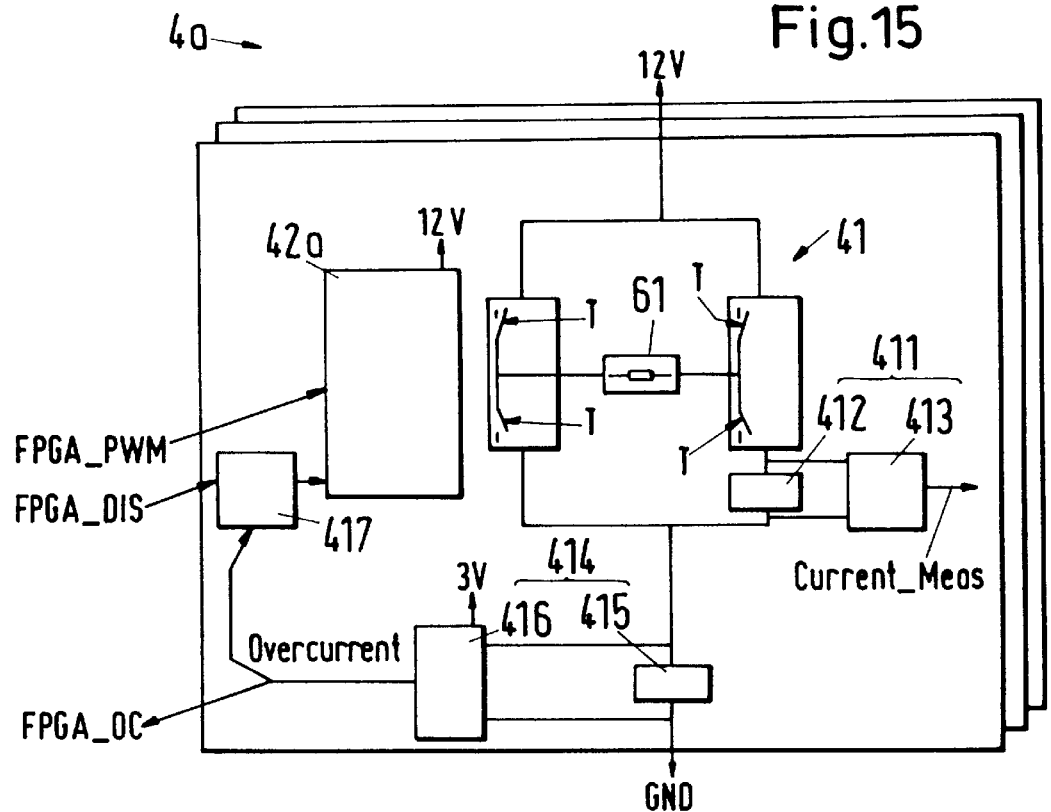
Figure 16:
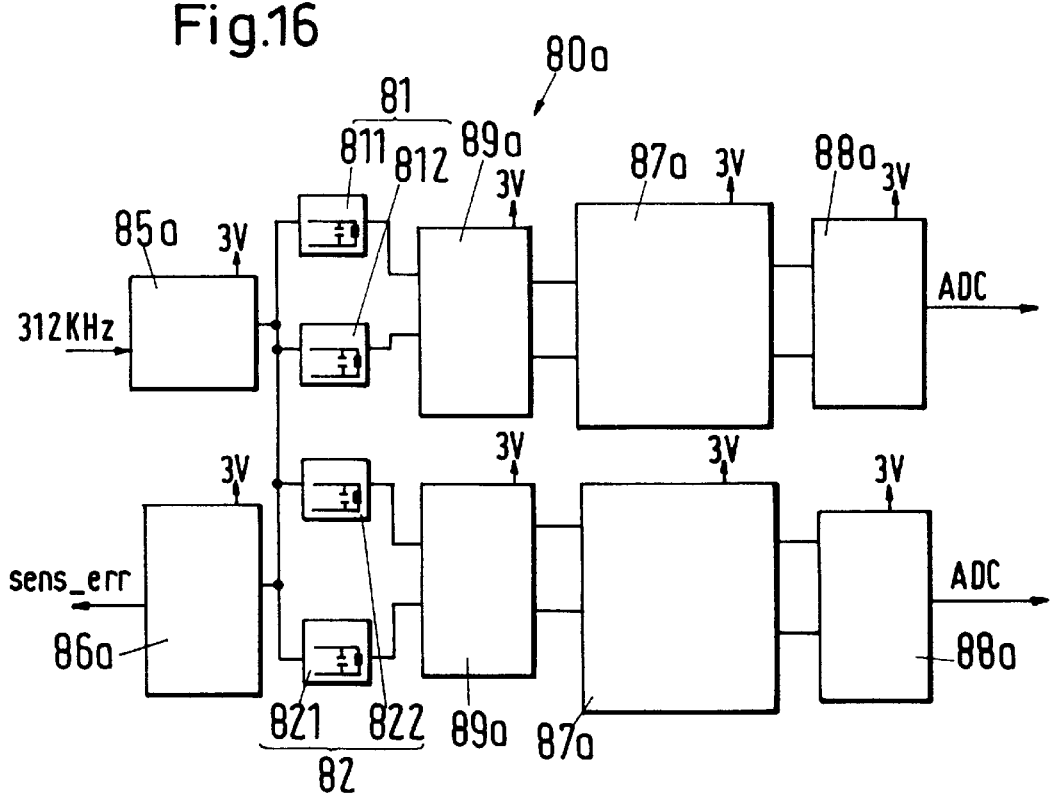
Figure 17:
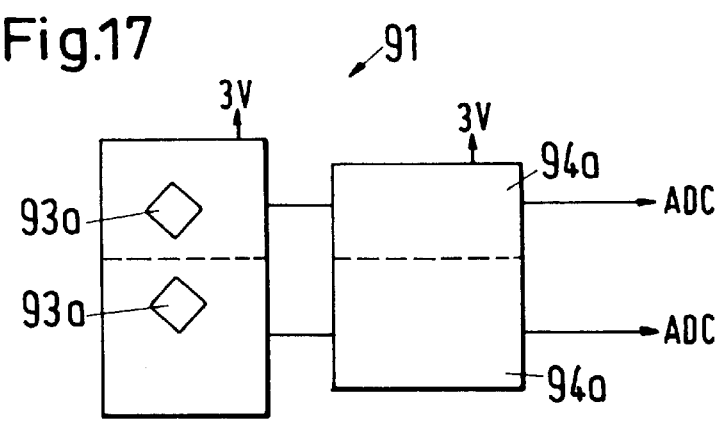
Figure 18:
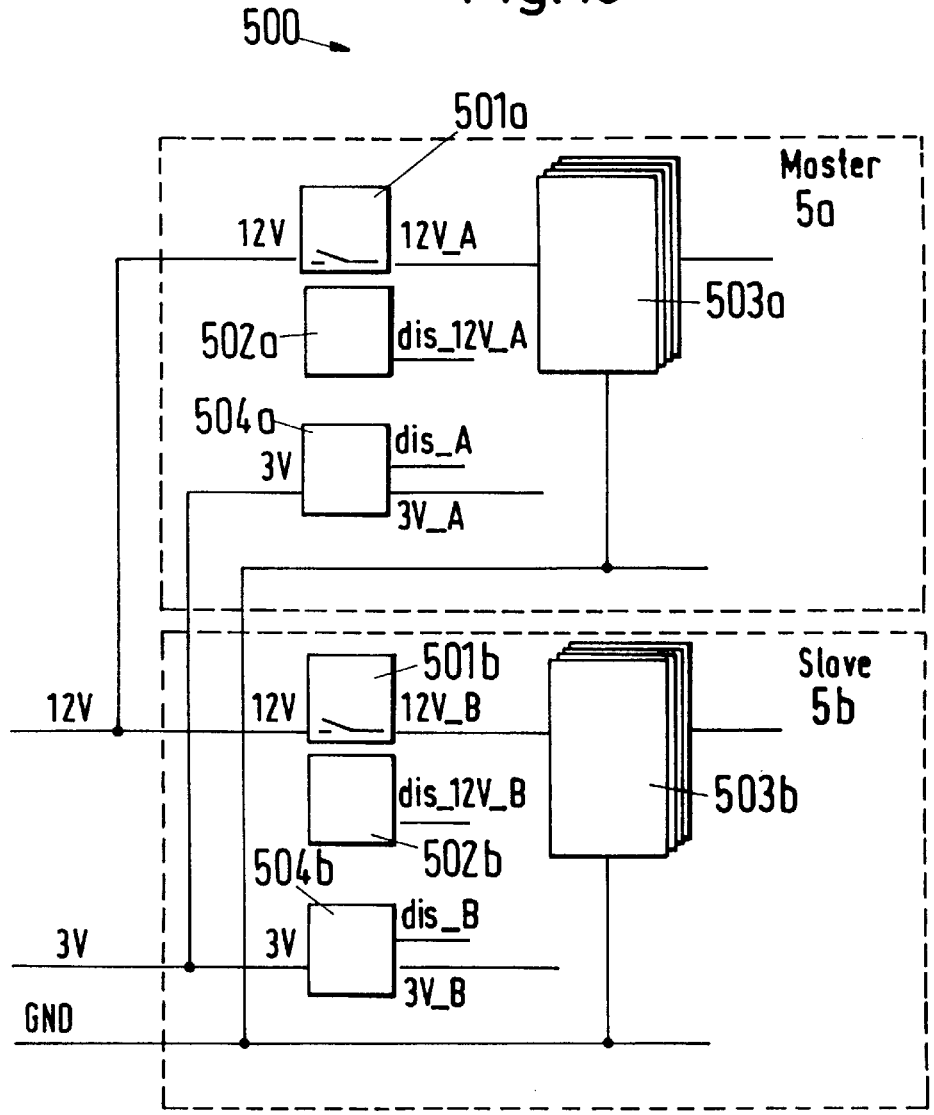
Figure 20A:
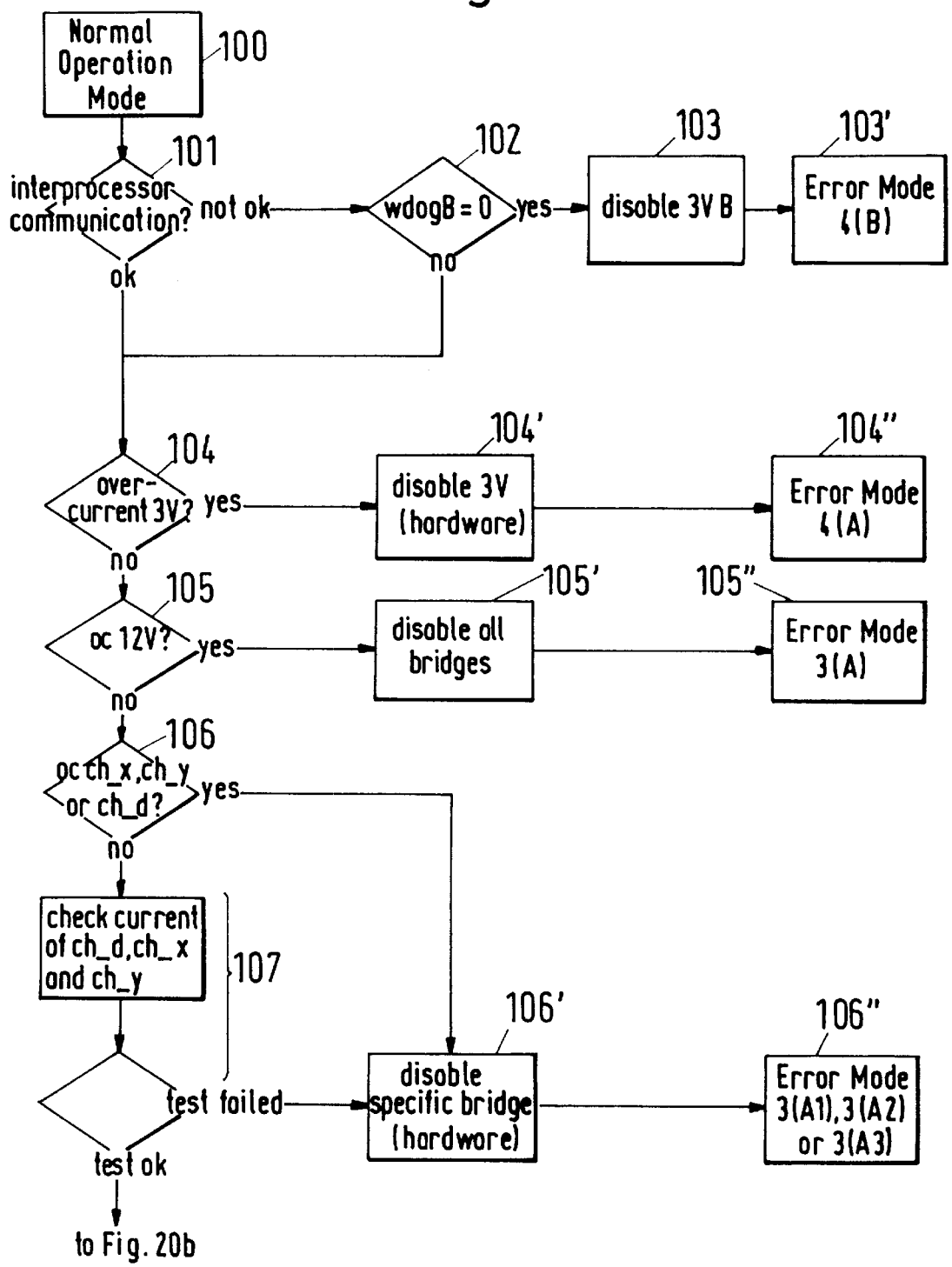
Figure 20C:
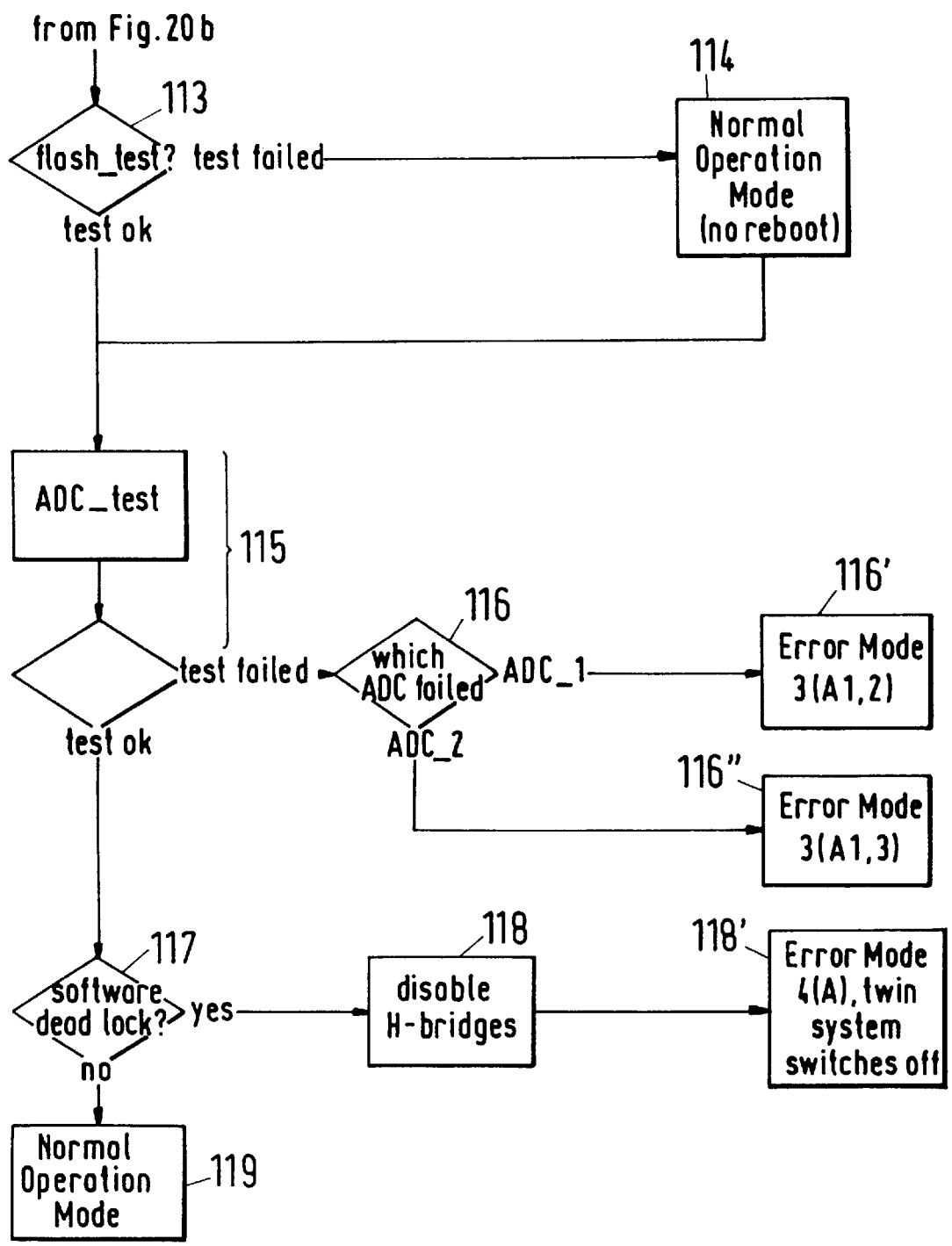

The invention will be explained in the following in more detail with reference to exemplary embodiments and with reference to the drawings. Shown in the schematic drawings are:

FIG. 1: a schematic illustration of a first exemplary embodiment of the rotary drive in accordance with the invention, FIG. 2: the stator and the rotor of the first exemplary embodiment in a plan view (rotor sectioned), FIG. 3: a section through the stator of FIG. 2 along the section line III—III in FIG. 2, FIG. 4: a schematic illustration of the arrangement and of the connecting together of the control coils, FIG. 5: a schematic illustration of the arrangement and of the connecting together of the drive coils, FIG. 6: an exemplary embodiment of a bipolar power amplifier, FIG. 7: the stator of a variant of the first exemplary embodiment in a plan view, FIG. 8: as in FIG. 4, however for the variant in accordance with FIG. 7, FIG. 9: a perspective illustration of a second exemplary embodiment of the rotary drive in accordance with the invention, designed as a temple motor, partly in section, FIG. 10: analogously to FIG. 2, however for a third exemplary embodiment of the rotary drive, FIG. 11: a block diagram of an exemplary embodiment of a control apparatus, FIG. 12: a block circuit diagram of a signal processing and regulation device of the control apparatus in accordance with FIG. 11, FIG. 13: a block diagram of an FPGA logic, FIG. 14: a block diagram of inter-processor connections, FIG. 15: a block diagram of a power component, FIG. 16: a block diagram of a two-axis measurement system, FIG. 17: a block diagram of a field sensor, FIG. 18: a block diagram of a supply circuit, FIG. 19: a flow chart of a software cycle, FIGS. 20a–c: a flow chart of a fault detection routine, and FIG. 21: a schematic sectional illustration of an exemplary embodiment of a blood pump in accordance with the invention.

FIG. 1 shows in a schematic block diagram the essential parts of a first exemplary embodiment of the rotary drive in accordance with the invention, which is designed as a bearingless motor and is provided in its entirety with the reference symbol 1. The rotary drive 1 comprises a stator 2, a permanent-magnetic rotor 3 and a control apparatus 5 with a setting device 4 comprising a plurality of bipolar power amplifiers 41. The control device 5 further comprises the totality of control and regulation units which are required for the operation of the rotary drive 1. The latter are not illustrated in detail in FIG. 1 for the sake of clarity. The construction of the control apparatus 5 will be described in detail below.

The stator 2 and the rotor 3 are illustrated in FIG. 2 in a plan view and in FIG. 3 in a section along the line III—III in FIG. 2.

FIG. 3 illustrates in addition the definition of a stator system, to which reference will be made in the description. The stator system is a Cartesian coordinate system with the axes X, Y and Z, the origin of which lies at the center of the stator and which is stationary with respect to the stator 2. In accordance with convention the Z axis points in the direction of the desired axis of rotation of the rotor 3, with that axis of rotation A being meant, about which the rotor 3 rotates in the operating state when it is located in an exactly centered position (desired position) with respect to the stator 2, and is thus in particular also not tilted. The direction of the Z axis will be designated in the following as the "axial direction". The direction of the X and the Y axes of the stator system is arbitrary. The X-Y plane, which is spanned by the X and the Y axis, is the plane in which the rotor 3 rotates if it is not tilted or deflected in the axial direction. The position of the rotor 3 (or, respectively, of its center) with respect to the X-Y plane will be designated in the following as its "radial position".

In accordance with the principle of the bearingless motor, the stator 2 comprises a drive winding 6 for producing a magnetic drive field which produces a torque on the rotor 3 and drives the latter, as well as a control winding 7 for producing a magnetic control field by means of which the radial position of the rotor 3 can be regulated. Through the combination of these two rotary magnetic fields the rotor 3 can be driven and magnetically journalled without contact in the stator 2 without separate magnetic bearings being necessary for this. In the bearingless motor three degrees of freedom of the rotor, namely its rotation about the axis of rotation A and its radial position (two degrees of freedom) are actively magnetically controlled or regulated respectively. With respect to three further degrees of freedom, namely its deflection in the axial direction and tiltings relative to the Z axis (two degrees of freedom) the rotor is passively magnetically, that is, not in a controlled manner, stabilized through reluctance forces. Further details with respect to the method of functioning of the bearingless motor and its regulation and control are disclosed in the already cited specifications WO-A-96/31934, WO-A-95/18925 and WO-A-98/11650 and will therefore not be explained further here.

In the first exemplary embodiment the drive winding 6 has two loops 61, 62, which in each case belong to a different drive phase, which means that the drive winding 6 is designed to be two-phased (with two drive phases). The control winding 7 has four loops 71, 72, 73, 74, which in each case belong to a different control phase, which means that the control winding is designed to be four-phased (with four control phases).

The stator 2 comprises a plurality of, in the first exemplary embodiment eight, stator teeth 21–28, which are magnetically coupled to one another by means of a yoke 20, usually an iron yoke. The drive and the control winding 6 and 7 respectively are wound around the stator teeth 21–28 in the form of discrete coils. In this a plurality of discrete coils can be electrically connected to one another in a parallel or in a series circuit. The term "loop" is used in each case to mean the totality of all the discrete coils which are electrically connected together in parallel or in series. Naturally a loop can also comprise only one discrete coil. The term "phase" designates in each case one loop and the part of the setting device 4 which supplies it, here in particular the power amplifier 41 which supplies this loop with a phase current or with a phase voltage as a setting parameter. The setting device 4 can be formed as a current controller or as a voltage controller for the drive and the control winding 6, 7. Since in practice current regulations are mainly used, reference is made in the following to the case in which the setting parameters are phase currents. For voltage regulations with phase voltages as a setting parameter the same explanations hold analogously.

As FIG. 2 shows, the two-phase drive winding 6 in the first exemplary embodiment consists of four concentrated coils, which will be designated in the following as drive coils 611, 621. The two drive coils 611 form the one loop 61 of the drive winding 6, whereas the two drive coils 621 form the other loop 62 of the drive winding 6. Drive coils belonging to the same drive phase are designated by identical reference symbols. Each drive coil 611, 621 is wound as a concentrated coil in each case around two directly adjacent stator teeth 21–28 in such a manner that none of the stator teeth 21–28 carries more than one drive coil 611, 621. This means that the first drive coil 611 is wound around the first and second stator tooth 21 and 22 respectively, the next drive coil 621 around the third and fourth stator tooth 23 and 24 respectively, the next drive coil 611 around the fifth and sixth stator tooth and 26 respectively and the last drive coil 621 around the seventh and eighth stator tooth 27 and 28. The drive coils 611, 621 are connected together in such a manner that in each case two diametrically oppositely lying drive coils 611 or 621 form a loop 61 or 62 of the drive winding 6 and thus belong to the same drive phase. The distribution of the drive coils 611, 621 over the stator teeth 21–28 and their connection to form the two loops 61, 62 of the drive winding is clarified once again in FIG. 5 in a rather schematic illustration, with the loop 61 of the first drive phase being illustrated in the upper part of FIG. 5 and the loop 62 of the second drive phase in the lower part of FIG. 5.

FIG. 2 likewise shows the four-phase control winding 7, which comprises eight concentrated coils, which will be designated in the following as control coils 711, 721, 731, 741. Each control coil 711, 721, 731, 741 is wound around a different stator tooth 21–28, which means that each stator tooth carries exactly one control coil. In each case two control coils 711 or 721 or 731 or 741 form a loop 71 or 72 or 73 or 74 of the control winding 7 and thus belong to the same control phase. The control coils belonging to the same control phase are designated by identical reference symbols. The control coils are connected together in such a manner that in each case the control coil which is wound around a first stator tooth and the control coil which is wound around the next but one stator tooth when viewed in the peripheral direction of the stator belong to the same control phase. This connection of the individual control coils 711, 721, 731, 741 is clarified in FIG. 4 in a schematic illustration. The control coil 711, which is wound around the first stator tooth 21 (FIG. 4, above) and the control coil 711, which is wound around the third stator tooth 23, are connected together and form the loop 71 of the first control phase of the control winding 7. The two control coils 721 on the fifth and seventh stator tooth and 27 respectively form the loop 72 of the second control phase. The two control coils 731 on the second and fourth stator tooth 22 and 24 respectively form the loop 73 of the third control phase (FIG. 4, below), and the two control coils 741 on the sixth and eighth stator tooth 26 and 28 respectively form the loop 74 of the fourth control phase.

With this design of the drive and control phases the drive winding has a number of pole pairs equal to one and the control winding a number of pole pairs equal to two. In general those designs are preferred for the rotary drive 1 in accordance with the invention in which the numbers of pole pairs of the drive winding and of the control winding differ by one, which means that if p designates the number of pole pairs of the drive winding, then the control winding preferably has the number of pole pairs p±1, that is, either p+1 or p−1. For practical reasons, designs are preferably preferred in which the number of pole pairs of the drive winding is p=1 or p=2 or p=3 and the number of pole pairs of the control winding amounts to one or two or three.

In accordance with the invention the setting device 4 (FIG. 1) is designed in such a manner that the phase current (or the phase voltage) can be regulated as a setting parameter for each loop 61, 62 of the drive winding and for each loop 71–74 of the control winding independently of the phase currents (or phase voltages) for the other loops. For this the setting device comprises in the first exemplary embodiment six separate bipolar power amplifiers 41, namely one for each of the two drive phases and one for each of the four control phases. Through this it is ensured that even in the event of the failure of a complete drive and/or control phase the remaining fault-free phases can continue to be operated without restriction.

In a preferred design the bipolar power amplifiers 41 are in each case H-bridge switching amplifiers. FIG. 6 shows the electrical circuit diagram of such a power amplifier 41, which supplies one of the phases (here the loop 61 of the drive winding) with the phase current. The power amplifier 41 is equipped in a manner which is known per se with the switching transistors T and recovery diodes F and is operated with the two operating potentials + and −, with the operating potential− for example being the ground potential GND and the operating potential +0 being a potential of +12V. The switching transistors T are preferably field effect transistors (FETs) and in particular MOS-FETs. A current measurement device 411 is provided for measuring the respective phase current.

Naturally other types of power amplifiers 41 and/or setting devices 4 can also be provided in the rotary drive 1. For example the individual power amplifiers can also be realized as bridge branches of a multiple-phase current controller and a plurality of phases can be connected together in a star circuit, with it then however being necessary for the star point to lie at a loadable potential in order to ensure the independent regulation of the individual phase currents. A loadable star circuit of this kind is disclosed for example in the European patent application no. 99810553.0 of the present applicant and will therefore not be discussed here in detail. Other forms of switching amplifiers or analog amplifiers can however also be used. It is however important that the power amplifier 41 be designed in such a manner that that it can be bipolarly operated, by which is meant that both the phase currents and the phase voltages can take on positive and negative signs. In addition the setting device 4 must be able to supply each drive and each control phase with a setting parameter (phase current or phase voltage respectively) which can be regulated independently of the setting parameters for the other phases.

The permanent-magnetic rotor 3 of the rotary drive 1 (see FIG. 2 and FIG. 3) is bipolarly (number of pole pairs equal to one) diametrically magnetized and is designed as a ring-shaped rotor 3 with a permanent-magnetic ring 31 and an iron yoke 32 which is arranged to lie radially inwardly with respect to the ring 31. The magnetization of the rotor is symbolically illustrated in FIG. 2 by the arrow M. Naturally other numbers of pole pairs and other forms of the rotor magnetization are also possible. The rotor 3 can in particular also be designed in the shape of a disc.

For determining the radial position of the rotor 3 in the stator 2 at least two, in this exemplary embodiment four position sensors 81, 82, 83, 84 (see FIG. 1) are provided, of which in each case two, namely the position sensors 81, 82 and the position sensors 83, 84 respectively, belong to a two-axis measurement system 80a, 80b (see FIG. 11) by means of which the radial position of the rotor 3 can be determined. Since two independent measurement systems for the radial position of the rotor are thus present, the position measurement of the rotor 3 is designed to be redundant, through which the fault tolerance of the rotary drive 1 is increased. This will be explained further below Each position sensor 81–84 preferably comprises two sensor elements 811, 812 and 821, 822 and 831, 832 and 841, 842 respectively (see FIG. 2). Each sensor element is arranged in a groove between two adjacent stator teeth 21–28 so as to lie oppositely to the rotor 3, so that exactly one sensor element is located in each of the eight grooves. The sensor elements can either be arranged in the X-Y plane or slightly axially displaced with respect to the latter. In each case two sensor elements 811, 812 and 821, 822 and 831, 832 and 841, 842 respectively which belong to the same position sensor 81 and 82 and 83 and 84 respectively are arranged to be displaced with respect to one another with respect to the peripheral direction of the stator 2 by 180°, so that they lie diametrically oppositely in the stator 2 (see FIG. 2). Through an arrangement of this kind systematic faults such as common mode disturbances, offsets, drifts, in particular thermal drifts in the position sensors 81–84, can be eliminated in that in each case the difference signal of the two signals of the sensor elements which belong to the same position sensor 81–84 are used for the determination of the rotor position.

The two position sensors which belong to the same two-axis measurement system, thus e.g. the two position sensors 81 and 82 with their four sensor elements 811, 812, 821, 822, are displacedly arranged relative to one another by approximately 90° with respect to the peripheral direction of the stator and by approximately 45° relative to the position sensors 83, 84 of the other two-axis measurement system.

All types of distance sensors which are known per se are suitable as sensor elements 811–842, in particular eddy current sensors, inductive sensors, magnetic field probes such as Hall sensors, optical sensors and capacitive sensors. The sensor elements are preferably eddy current sensors.

For the control and regulation of the bearingless motor (drive and position of the rotor 3), which usually takes place by means of a vector regulation or of a field oriented regulation method respectively, it is necessary to know the direction of the rotor magnetization, which means the momentary position of the magnetization of the rotor 3 relative to the X-Y plane of the stationary stator system. This parameter is usually designated as the rotor field angle. In practice, the latter differs only slightly from the geometrical rotor angle. In the following therefore this difference will no longer be considered, and the rotor angle will be spoken of for short, with this term comprising both the geometrical rotor angle and the rotor field angle. At least one field sensor is provided for determining the rotor angle. In order to design the rotary drive 1 redundantly with respect to the determination of the rotor angle as well, two independent field sensors 91, 92 are provided. Each field sensor 91, 92 comprises two magneto-resistive field measurement bridges, with the magneto-resistive elements for example being giant magnetoresistive (GMR) elements.

Each of the field sensors 91, 92 delivers e.g. in each case the sine and the cosine of the field that it senses, from which the rotor angle can be determined. Thus two independent systems are present, by means of which in each case the rotor angle can be determined. As FIG. 3 shows in particular, the field sensors 91 and 92 are axially displaced with respect to the X-Y plane, namely are arranged beneath the rotor 3 as in the illustration. For further details of the determination of the rotor angle by means of field sensors 91, 92 which are arranged in this manner, reference is made to the European patent application no. 99810634.8 of the present applicant, which has as a subject matter a sensor arrangement for determining the direction of the rotor magnetization.

It is self evident that other means for determining the rotor angle can also be provided instead of or in supplement to the field sensors 91, 92 which are explained here.

In the normal operating state of the rotary drive 1 the magnetic drive field is produced by means of the two-phase drive winding 6, which exerts a torque on the rotor 3 and sets the latter into rotation. By means of the four-phase control winding 7 the radial position of the rotor 3, which can be determined with the help of the position sensors 81–84, is regulated. Numerous designs for the position regulation of the rotor 3 are known from the literature. Several regulation structures are described especially for the bearingless motor e.g. in WO-A-95/18925. Therefore the design of the regulation of the bearingless motor will not be further discussed here.

If now a failure of a control phase and/or the failure of a drive phase arises during operation, then the rotary drive 1 in accordance with the invention can continue to be correctly operated with a reduced number of drive phases and/or control phases since the phase current for each individual drive phase and for each individual control phase can be regulated completely independently of the other phase currents. Since the minimum requirement for a reliable driving and for a reliable magnetic journalling of the rotor is that at least one drive phase and at least two control phases work without fault, one drive phase and two control phases can completely fail or be deactivated respectively in the extreme case in the first exemplary embodiment without the rotary drive 1 losing its capability of functioning. The treatment of the faults will be discussed further below. For further details of the fault tolerance with respect to the journalling function on the one hand and to the drive function on the other hand, reference is made here to the two European patent applications no. 99810760.1 and no. 99810553.0 of the present applicant, the disclosures of which are hereby declared to be an integral constituent of this application.

If only one drive phase remains fault-free, then the rotary drive 1 works in accordance with the principle of the single phase a. c. motor. In this case as long as the rotary drive 1 is not stopped, it continues to rotate, that is, to work correctly. If such a single phase a. c. motor is stopped, however, it is possible depending on the position of the rotor 3 relative to the stator 2 that the rotary drive 1 can not be started again without further ado. It is then possible however, through a corresponding activating of the still fault-free control phases, to rotate the rotor 3 until the rotor 3 is in a position in which it can be started with one drive phase. As soon as the rotor 3 is again rotating, operation with only one drive phase and at least two control phases can then be maintained.

The problem of starting up with only one drive phase can also be helped in that the stator 2 is designed in such a manner that when stopped the rotor 3 comes to rest in a predetermined "rest position" which is chosen in such a manner that the rotor 3 can start up again from this rest position. This measure is sufficiently known from single phase a. c. motors and will therefore not be explained further here.

FIG. 7 shows in a plan view the stator 2 of a variant of the first exemplary embodiment. In the following only the differences will be discussed in more detail. In this variant, with likewise four control phases and two drive phases, the control winding comprises a total of sixteen concentrated control coils 711, 721, 731, 741, with in each case two control coils being provided on each stator tooth 21–28. In each case four control coils, which are wound around four is different stator teeth, are connected together to form a loop 71–74 of the control winding and thus belong to the same control phase (these control coils again have in each case identical reference symbols). The connections between the individual control coils can be found in the schematic illustration in FIG. 8. The first loop 71 (see FIG. 8 above) of the control winding is realized through the connecting together in each case of one of the two control coils which are arranged on the first, third, fifth and seventh stator tooth 21, 23, 25, 27. These control coils are designated with the reference symbol 711. The second loop 72 of the control winding is realized through the connecting together of the respective other control coils on the first, third, fifth and seventh stator tooth 21, 23, 25, 27, which thus do not belong to the first loop 71. These control coils are designated by the reference symbol 721. The control coils 721 of the second loop 72 are thus located on the same stator teeth as the control coils 711 of the first loop 71. The first and the second loop are thus substantially realized through an identical arrangement and connecting together of their respective control coils.

Analogous remarks hold for the control coils of the third and fourth loop 73 and 74, which are designated by the reference symbols 731 and 741 respectively (FIG. 8 below). These are in each case arranged on the second, fourth, sixth and eighth stator tooth 22, 24, 26, 28.

The control coils are thus connected together to form the individual loops of the control winding in such a manner that when viewed in the peripheral direction of the stator 2 the control coils which are in each case wound around directly adjacent stator teeth belong to different loops of the control winding.

The in each case two control coils which are arranged on the same stator tooth can be arranged adjacently, as is illustrated in FIG. 7. Preferably, in particular in the constructional form of the temple motor to be discussed further below, the two control coils which are wound around the same stator tooth are in each case wound one on the other, so that the outer control coil surrounds the inner control coil. This arrangement is schematically shown in FIG. 8. The four control coils which are connected together to form the same loop of the control winding are always only the outer or only the inner control coils. Thus e.g. the control coils 711 of the first loop 71 are only outer coils, whereas the control coils 721 of the second loop are only inner coils. The individual control coils are preferably constructed in such a manner that the ohmic resistance of the loop which is formed by the outer control coils, e.g. loop 71, is either equal to (symmetric design) or greater than (asymmetric design) the ohmic resistance of the loop which is formed by the inner control coils, e.g. loop 72.

The two-phase drive winding is designed in the same manner that is illustrated in FIG. 5 and has already been explained in connection with the first exemplary embodiment.

The design of the control winding which is shown in FIG. 7 and FIG. 8 has the following advantage: In normal operation the position of the rotor is regulated with all four control phases, that is, with all sixteen control coils. Since two control coils are arranged on each stator tooth, only half the current need in each case flow through them which would be necessary to produce the same field with only one control coil on this stator tooth. Twice half the current is however more favorable from the point of view of the losses than once the whole current. If now one control phase fails, for example the first loop 71, then this can be simply compensated in that the phase current in the loop 72 of the second control phase is doubled. This takes place automatically through the regulation. Through this design with two control coils per stator tooth which belong to different control phases and which are both active in normal operation, a hot redundancy is realized. The "emergency system" is already active in normal operation, and the fault need not first be detected before it can be compensated.

FIG. 9 shows in a perspective illustration and partly in section a second exemplary embodiment of the rotary drive 1 in accordance with the invention which is designed as a so-called temple motor. A temple motor is disclosed for example in the already cited WO-A-98/11650 (see FIG. 8k there and the associated text passages). The stator 2 of the temple motor has a plurality of, here eight, stator teeth 21–28 which are connected by a yoke (In FIG. 9 only six stator teeth 21–25, 28 can be recognized). The yoke 20, which couples the stator teeth 21–28 magnetically to one another, is manufactured of a ferromagnetic material, preferably iron. Each stator tooth 21–28 is designed in L shape with a longer limb SL and a shorter limb SK. The longer limb SL extends in each case in the axial direction and the shorter limb SK extends radially inwardly, that is, in the direction towards the rotor. The drive and control coils 611, 621, 711, 721, 731, 741 are wound around the longer limb SL of the stator teeth 21–28. The embodiments of the stator in accordance with FIG. 2 and FIG. 7 ("planar" design) on the one hand and FIG. 8 (temple motor) on the other hand can be controlled in the identical manner, are functionally equivalent, in particular as regards their electrical method of operation, and have in particular the same effect on the permanent-magnetic rotor 3. The L-shaped stator teeth 21–28 are equivalent as regards their principle of operation to the "straight" stator teeth 21–28 as they are shown in FIG. 2 and FIG. 7.

The winding, arranging and connecting up of the drive coils 611 and 621 is the same as is shown in FIG. 5 and has already been explained. The loops 71–74 of the control phases can be designed either with eight discrete control coils 711, 721, 731, 741, that is, one per stator tooth, which are arranged and connected up as shown in FIG. 4, or with sixteen discrete control coils 711, 721, 731, 741, that is, two per stator tooth, which are arranged and connected up in accordance with FIG. 8. In the variant with two control coils per stator tooth these two control coils can be wound adjacently with respect to the axial direction, or, as is preferable, one on the other, as has already been explained above. The temple motor in accordance with FIG. 9 with four control phases and two drive phases is functionally equivalent to the first exemplary embodiment or to its variant respectively. The explanations of this point also hold analogously for the design as a temple motor in accordance with FIG. 9.

Naturally the temple motor can also be equipped with a different number of stator teeth and/or with a differently designed drive winding and/or control winding. The position sensors and the field sensors are not illustrated in FIG. 9. If the rotary drive in accordance with the invention is part of a blood pump, then it is preferably designed as a temple motor, as will be discussed further below.

FIG. 10 clarifies in an illustration corresponding to FIG. 2 a third exemplary embodiment of the invention in which the rotary drive 1 has exactly three drive phases and exactly three control phases. In the following only the differences from the first two exemplary embodiments will be discussed in more detail. Otherwise the above explanations also hold in an analogous manner for the third exemplary embodiment. In particular parts which are identical or have equivalent functions will be designated by the same reference symbols.

In the third exemplary embodiment the stator 2 has twelve stator teeth 21–29, 210, 211, 212, between which the rotor 3 can be magnetically journalled. Corresponding to the three drive phases the drive winding has three loops, each of which is realized through the connecting together of two discrete drive coils 611, 621, 631. Thus six drive coils 611, 621, 631, which are designed in each case as concentrated coils, are provided in all. Each drive coil 611, 621, 631 is wound around two in each case directly adjacent stator teeth, analogously as has been explained in connection with FIG. 2. In each case the two diametrically oppositely lying drive coils 611 and 621 and 631 respectively are connected together to form one loop of the drive winding, which means that the two drive coils which are provided with the reference symbol 611 form the first loop of the drive winding, the two drive coils which are provided with the reference symbol 621 form the second loop of the drive winding and the two drive coils which are provided with the reference symbol 631 form the third loop of the drive winding.

The three-phase control winding comprises twelve discrete control coils 711, 721, 731, which are designed as concentrated coils, and of which in each case four control coils form one loop of the control winding, that is, belong to the same control phase. One control coil is provided on each stator tooth 21–212. The four control coils which are designated by the reference symbol 711 and which are wound around the first, fourth, seventh and tenth stator tooth 21, 24, 27, 210 respectively are connected together to form the loop of the first control phase; the four control coils which are designated by 721 and which are wound on the second, fifth, eighth and eleventh stator tooth 22, 25, 28, 211 respectively form the loop of the second control phase; and the four control coils which are designated by 731 and which are wound on the third, sixth, ninth and twelfth stator tooth 23, 26, 29, 212 respectively form the loop of the third control phase.

The number of pole pairs of the drive winding is p=1 and the number of pole pairs of the control winding is equal to two, that is, equal to p+1.

The position sensors (not illustrated in FIG. 10) are preferably arranged in each case between two adjacent stator teeth in the same manner as has already been explained above. The field sensors (not illustrated in FIG. 10) are preferably arranged to be axially displaced with respect to the X-Y plane below or above the rotor 3 analogously as is shown in FIG. 2 and FIG. 3.

It is self evident that in the third exemplary embodiment as well, the setting device 4 (FIG. 1) for the supplying of the individual loops of the drive and of the control winding is designed in such a manner that each drive phase and each control phase can be controlled and operated respectively completely independently of the other phases. A separate bipolar power amplifier 41 (FIG. 1, FIG. 6) is preferably provided here as well for each of the three loops of the drive winding and for each of the three loops of the control winding, so that the phase current (or the phase voltage) for each loop of the drive winding and for each loop of the control winding can be regulated independently of the phase currents (or the phase voltages) for the other loops. For further details of the fault-tolerant design with three drive phases and with three control phases respectively, reference is made to the two already cited European patent applications no. 99810553.0 and no. 99810760.1.

It is self evident that the third exemplary embodiment can also be designed as a temple motor (see FIG. 9).

In deviation from the exemplary embodiments described here, it is also possible to design the control coils and/or the drive coils in the form of distributed windings.

In principle any control apparatus by means of which a bearingless motor can be operated is suitable as a control apparatus 5 (FIG. 1), provided the control apparatus 5 is modified in such a manner that it enables a completely independent controlling and bipolar operation of each individual drive phase and each individual control phase.

In the following however another particularly preferred exemplary embodiment for the control apparatus 5 will be described which is also distinguished by its additional high fault tolerance. In this, reference is made to the case in which the drive winding 6 is designed to be exactly two-phased and the control winding 7 exactly four-phased. This is however not a necessary assumption. This control apparatus 5 can also be designed analogously for different numbers of drive phases and/or control phases.

FIG. 11 shows in a block diagram the principles of the construction of the exemplary embodiment of the control apparatus 5, with communication connections or connections for the signal and data transfer as well as supply connections being indicated in each case by arrows. The control apparatus comprises two nearly identical control systems 5a, 5b, each of which can operate the bearingless motor 1 (illustrated here symbolically as a blood pump 10)

alone and independently of the other control system. In the normal fault-free operating state, both control systems 5a, 5b are active and together regulate the operation of the bearingless motor 1. In the event of a fault, however, each of the two control systems can immediately control and regulate the operation of the bearingless motor 1 alone, which means that the correct operation of the motor 1 is possible both with respect to the drive and with respect to the journalling with only one of the two control systems 5a, 5b. This hot redundancy signifies a considerable increase in the operating reliability, which is a great advantage in particular for blood pumps.

Depending on the fault which arises, it is however also possible to deactivate only a part of a control system 5a, 5b, which will be explained further below.

In the short run, which means for a time duration of at least three milliseconds, the bearingless motor can continue to operate without greater disturbances, for example a physical contact between the rotor and stator, arising even when both control systems 5a, 5b fail. This has the advantage that in the event of a failure of both control systems 5a, 5b there is enough time remaining to start at least one of the two control systems 5a, 5b anew through a reset; since only a time of approximately one millisecond is typically required for a reset of this kind. If the reset is successful for at least one control system, then the correct operation can be continued.

One of the two control systems 5a, 5b, here the control system 5a, is operated as a master and the other control system 5b as a slave. Each control system 5a, 5b comprises at least the following components: at least two position sensors 81, 82 and 83, 84 respectively, which form in each case a two-axis measurement system 80a, 80b for determining the radial position of the rotor 3; means for determining the rotor angle which here comprise at least one field sensor 91, 92 per control system; at least three separate power amplifiers 41 which are provided in a power component 4a, 4b for supplying the individual loops of the drive and of the control winding; and a signal processing and regulation device 50a, 50b, which processes the sensor signals, carries out the regulation of the drive and of the position of the rotor, and controls the power component 4a, 4b with the power amplifiers 41. The power amplifiers 41 of each control system 5a, 5b control at least one drive phase and at least two control phases, so that each control system can operate the bearingless motor 1 alone. The power component 4a supplies for example the loop 61 (see FIG. 5) of the drive winding 6 as well as the two loops 71, 73 (see FIG. 4 and FIG. 8) of the control winding 7, whereas the power component 4b feeds the loop 62 of the drive winding 6 and the two loops 72, 74 of the control winding 7. Each control system thus in each case controls one of the loops 71, 72 of the control winding, which are illustrated in the upper half of FIG. 4 and of FIG. 8 respectively, and one of the loops 73, 74 of the control winding, which are illustrated in the lower half of FIG. 4 and of FIG. 8 respectively. Each control system 5a, 5b is supplied with two voltages, here a regulated d. c. voltage of 3V ($3V_{13}A$ and 3V__B respectively) and a d. c. voltage of 12V ($12V_{13}A$ and $12V_{13}B$ respectively).

Since the signal processing and regulation device 50a, 50b is usually realized on a chip or an electronic print respectively, it will be designated in the following for short as a DSP board (DSP: Digital Signal Processor). The remaining components of the control systems 5a, 5b are also preferably realized in the form of electronic prints or chips respectively, as the illustrations in particular in FIGS. 11, 15–18 indicate.

Individual components can be switched off in both control systems 5a, 5b, through which a large number of faults can be reacted to, and indeed while retaining the still possible operating conditions which are ideal for the respective fault. In order that the control apparatus 5 can react ideally to the various fault states in each case, each control system 5a, 5b has available the process and system data which are required for operation (software etc.). In addition the two control systems 5a, 5b can exchange signals with one another and can monitor and check up on one another via a parallel or serial data bus.

During the fault-free normal operation the two control systems 5a, 5b can exchange synchronization signals with one another in order to synchronize the switching cycles of the power amplifiers 41 (H bridges) and the excitation frequencies of the position sensors with one another in order that no disturbances arise here. The connections for the exchange of the synchronization signals can be opened immediately in the event of a fault.

In the following the essential components of the control systems 5a, 5b will be described in detail.

FIG. 12 shows a block circuit diagram of the signal processing and regulation device 50a (DSP board) of the control system 5a (master), which is substantially identical to that of the control system 5b (slave). Thus the explanations also hold for the control system 5b. The letter "a" or "b" respectively at the end of a reference symbol indicates whether the designated element belongs to the master 5a or to the slave 5b respectively.

The DSP board 50a is responsible for the regulation of the position of the rotor 3 and of the phase currents for the drive and control phases, the reading and interpreting of all information and the sending of control signals to the various components. The DSP board 50a comprises a processor unit as a "brain", namely the digital signal processor (DSP) 51a. Furthermore, the following components are provided on the DSP board:

a logic which is provided with the reference symbol 52a and which is designated as the FPGA (Field Programmable Gate Array), a flash memory 53a, two analog/digital converters 54a (ADCs), a clock generator 55a, a linear regulator 56a, and a watchdog 57a. In addition, two inter-processor connections 58, 59 are provided as communication means and comprise in each case a driver or transceiver 581, 591a. The supply voltages are symbolically illustrated by the small arrows with the inscriptions 3V and 1.8V/3V respectively.

The entire system is supplied with energy in a manner which is known per se via a so-called transcutaneous energy transfer system (TETS). Data such as e.g. downloads or program changes can also be transmitted via the TETS. The TETS is connected to the DSP via a communication interface KS.

The DSP 51a, 51b is for example a processor of the type TMS320VC5402 from the Texas Instruments Company, which is e.g. clocked with 100 MHz or with 50 MHz. The DSP requires two supply voltages, namely 3V and 1.8V, the provision of which is yet to be discussed. The 3V voltage is required for the output pins, whereas the 1.8 V serve for the feeding of the core unit. The above named DSP 51a, 51b has a 16K×16 bit RAM memory with double access, which enables it to carry out the entire regulation program for the bearingless motor in the DSP 51a, 51b itself without accessing the external flash memory 53a, 53b.

The FPGA 52a, 52b contains the glue logic and serves for generating the pulse width modulation (PWM) with which the power amplifiers 41 are excited. The FPGA 52a, 52b is for example from the 42MX family of the Actel company, since these are very small (low space requirement) and in addition consume little energy. The FPGA 52a, 52b comprises on the one hand the glue logic which the DSP 51a, 51b requires for decoding addresses and for monitoring, and on the other hand a PWM generator 521a (see FIG. 13), which generates the PWM signals for triggering the switching transistors T (see FIG. 6) of the power amplifiers 41.

In FIG. 13 a block diagram of the FPGA 52a is illustrated in which the individual modules of the FPGA 52a of the master 5a are shown. The module address_decod communicates with the address bus of the DSP 51a (arrow "addr_bus") and decodes the addresses which are transmitted by the DSP 51a. The module FPGA_test is a counter which is clocked by the clock generator 55a of the same control system 5a (signal 5 MHz_A). The DSP 51a can read out this counter. If its value no longer changes, the DSP 51a decides that the FPGA 52a is faulty and switches into the corresponding fault mode (see further below). The module FPGA_watchdog is an internal watchdog for the FPGA 52a. This module is a resettable counter which is clocked by the clock generator 55b of the other control system 5b (signal 5 MHz_B) and is reset during each software cycle by a signal DSP_alive. The signal DSP_alive is generated by the DSP 51a of the same control system 5a. If this signal is absent, because for example the DSP 51a has failed or the software cycle is not run through correctly, then the module FPGA_watchdog generates a signal power_reset, which on the one hand temporarily switches off (dis_12V) the 12V supply of the power amplifiers 41 via a module power_enable (see below) and on the other hand sends a reset to the DSP 51a. After completion of the reset the 12V supply is switched back on. The entire reset process can be carried out in less than one millisecond, so that in the case of a successful reset no influencing of the correct journalling and drive function takes place.

The module syst_stat_in is a control word which can be modified only by the DSP 51a. Through the modification of specific bits of this word the DSP 51a can cause the switching off of the 3V supply voltage of the control system 5b (dis_B). Furthermore, the module syst_stat_in can in each case individually deactivate (dis_ch1, 2, 3) or activate its own phases, which means the individual power amplifiers 41 of those drive and control phases which are controlled by the control system 5a, via the module power_enable, which is connected to the module syst_stat_in. The power enable module can additionally deactivate (dis_12V) the entire 12V supply voltage of the power amplifiers 41 which are controlled by the control system 5a. The module syst_stat_out contains various information, e.g. whether, and if so, in which power amplifier 41 (H bridge) an excessive current is flowing (occh1, 2, 3), whether an excessive current is flowing in the 12V supply voltage of the power amplifiers 41, e.g. as a result of a short circuit (oc_ch12V), whether a faulty functioning in the excitation of the sensors of the control system 5a is present (sens_err_A) or whether the watchdog 57b of the other control system 5b reports a fault (wdog_B) which indicates that the DSP 51b of the other control system 5b is not or is no longer correctly working. The module FPGA_monoflop is a circuit which monitors the clock generator 55b of the other control system 5b (5 MHz_B) and produces a signal (clkB_alive) which indicates whether this clock generator 55b is still working. The module sens_sync synchronizes the excitation frequencies (5MHz_A, 5 MHz_B) for the position sensors of the two control systems 5a, 5b and has the synchronized excitation frequency (5 mhz_sens) as an output signal. This is divided by sixteen in the module clk_div_2 and provided as excitation frequency (312 kHz) for the position sensors. In the normal operating state the master 5a provides the clock signals for the measurement system (position and field sensors) of both control systems 5a, 5b. In the event of a fault, if e.g. this clock signal of the master 5a drops out, then the slave 5b must be able to fall back on its own clock generator immediately. This function is taken over by the module sens_sync, which is triggered by the clkB_alive signal of the FPGA_monoflop module. The module clk_div_1 divides the clock signal at its input (50 MHz_A), which is identical with the clock signal for the DSP 51a (50 MHz or 100 MHz clock frequency), by ten and by five and thus provides at its output the 5 MHz and a 10 MHz clock signal for the control system 5a (10 MHz_A, 5 MHz_A). The module cs_generator is a chip select generator which addresses the circuits of each control system so that the DSP 51 a can communicate with the latter via a bus.

The PWM generator 521a (module PWM_gen) is clocked with the 10 MHz clock frequency (10 MHz_A) and excites the individual switching transistors T (see FIG. 6) of the H bridges of the power amplifiers 41, in order thus to apply in each case the respective correct phase voltage to the associated loop of the drive or of the control winding. For each separate power amplifier 41 two outputs are provided at the PWM generator 521a (PWM_chx+ and PWM_chx−, with x=1 or 2 or 3), with the plus output triggering the upper switching transistors T in the illustration (FIG. 6) and the minus output triggering the lower switching transistors T. The PWM generator 521a furthermore contains a synchronization signal (PWM_sync) which ensures that the two PWM generators 521a, 521b of the master 5a and the slave 5b work synchronously and not against one another. The DSP 51a, which calculates the regulatory desired values for the phase voltages of the two control phases and of the drive phase, transmits these data via a data bus (data_bus) to the PWM generator 521a. The FPGA 52a also receives further data which it requires via this data bus.

The flash memory 53a, 53b is a CMOS non volatile memory, which operates with the supply voltage of 3V. The entire program for the operation of the bearingless motor is stored in it. The capacity of this flash memory 53a, 53b amounts to e.g. 256 K×16 bits. The flash memory 53a, 53b is required only when the entire system (the rotary drive 1 including the control apparatus 5) is started anew, when the DSP 51a, 51b completely reset, or when updates of the program are to be stored during operation. In the case of the new start or of a reset of the DSP 51a, 51b the entire program for the operation of the bearingless motor is loaded from the flash memory 53a via a bus into the internal RAM memory of the DSP 51a, 51b. If an update of the program is to take place during operation, then the latter is written into the flash memory 53a, 53b, while the DSP 51a, 51b still operates the rotary drive 1 with the older program version which is stored in its internal RAM. After the updated program has been completely loaded into the flash memory 53a, 53b, tested and validated, the DSP 51a, 51b receives a reset command and then takes over the new program from the flash memory 53a, 53b into its internal RAM memory in order to use it for the further operation. During normal operation the flash memory 53a, 53b is in a sleep mode, in which consumes almost no energy.

The two ADCs 54a, 54b, which are contained in the respective control systems 5a, 5b, are for example in each case four-channel analog/digital converters. Thus each control system 5a, 5b can read eight analog signals, with it being possible in each case to read two of them simultaneously. Of these eight analog inputs, three are used for the three phase currents of the three current measurement devices 411 in the H bridges of the three power amplifiers 41 (see FIG. 6), two for the two position signals of the two position sensors 81, 82 and 83, 84 respectively and two for the two signals (sine and cosine) of the field sensor 91 and 92 respectively. The remaining input can be used for other purposes. The ADCs 54a, 54b communicate with the DSP 51a, 51b via two serial connections, which are independent of the parallel data bus via which the two DSPs 51a, 51b communicate with one another and with the flash memory 53a, 53b, and are thus also independent of the FPGA 52a, 52b.

The clock generator 55a, 55b generates a clock frequency for the control system 5a, 5b by means of a crystal. The clock generator 55a, 55b is for example a parallel resonance crystal.

The linear regulator 56a produces the d. c. voltage of 1.8 V for the DSP 51a, 51b from the supply voltage of 3V. In principle DC-DC converters are also suitable for this. The latter admittedly consume somewhat less energy, but require however much more space on the electronic print than the linear regulator 56a. The latter is thus preferred.

The DSP 51a, 51b and especially the presence of the two voltages of 3V and 1.8 V is monitored with the watchdog 57a, 57b, for example of type TPS3305-18 from the Texas Instruments company. The watchdog 57a, 57b must be regularly triggered by the DSP 51a, 51b. If this signal fails to arrive, then a reset pulse is generated after a predetermined time of for example 1.6 seconds. The two DSPs 51a, 51b can monitor one another in the normal operating state by means of the watchdogs 57a, 57b. If one DSP, for example the DSP 51a, does not access the watchdog during a predeterminable time and triggers a reset, the other DSP 51b can measure this state and react to it. If the fault has not disappeared after the reset and again results in a reset, the supply voltage of the DSP 51a is switched off by the DSP 51b, through which the latter is deactivated.

The inter-processor connections 58, 59 with the drivers or transceivers 581, 591a, 591b are illustrated in FIG. 14 in a schematic block diagram. The signal designations entered there have the already explained meaning, with the letter A or B respectively at the end of the signal name designating the control system 5a or 5b respectively to which the respective signal relates. Thus e.g. wdog__A designates the signal of the watchdog 57a, which monitors the DSP 51a of the master 5a, whereas wdog__B designates the signal of the watchdog 57b, which monitors the DSP 51b of the slave 5b.

The inter-processor connections 58, 59, via which the two control systems 5a, 5b communicate with one another and via which they mutually monitor and control one another, comprise a data connection 58 (inter__data) and a control connection 59 (inter__control). In order that the two control systems can ideally cooperate in the fault-free normal operation and in order that they can react in an adapted manner to faults, each DSP 51a or 51b requires several items of information from the other DSP 51b or 51a, for example values for the position of the rotor, values for the rotor angle, information on the status of the respective other control system, clock and synchronization signals, the signals of the watchdog 57a and 57b respectively, and the possibility of deactivating the respective other control system. In this the data (values for the rotor position, for the rotor angle, etc.) are exchanged via the inter-processor connection 58 (inter__data), whereas the control signals for the communication are exchanged via the inter-processor connection 59 (inter__control). These inter-processor connections 58, 59 are mainly realized through connections (inter__control, inter__data) between the data/address bus 511a of the DSP 51a of the master 5a and an HPI (Host Port Interface) 512b of the DSP 51b of the slave 5b. The master 5a can read all required information from the program and data RAM of the DSP 51b of the slave 5b via these connections 58 and 59 respectively. In addition a connection 59' between the FPGAs 52a, 52b of the two control systems 5a, 5b is provided via which the two FPGAs 52a, 52b exchange control signals (dis__A,B; PWM__sync; 5 MHZ__A,B; wdog__A,B). In order to ensure a reliable functioning even in the event of the complete failure of a control system 5a or 5b, one of the drivers or transceivers 581, 591a, 591b which prevent a blocking of the data/address bus 511a or of the HPI 512b in the event of the complete failure of a control system 5a or 5b is provided in each physical inter-processor connection 58, 59, 59'. Otherwise e.g. a defective data bus pin or address bus pin of one of the two DSPs can pull this bus line to a state (high or low). In addition a serially connected resistance (not illustrated) is provided in each physical inter-processor connection 58, 59, 59', which protects the inputs and the outputs respectively of the individual control systems 5a, 5b against heavy short circuit currents.

FIG. 15 schematically shows the construction of the power component 4a, 4b, which comprises three subsystems, as indicated in FIG. 15, namely one for each power amplifier 41. In FIG. 15 only one of these subsystems is shown in detail. The subsytem of the power component 4a comprises the power amplifier 41, which is designed as an H bridge switching amplifier (see also FIG. 6), and here controls for example the loop 61 (symbolically indicated) of the drive winding. The switching transistors T are for example n-channel field effect transistors (FETs) with low drain source resistance $R_{DSon}$. In each case two FETs are arranged in a common very small housing. As a result of the low value of $R_{DSon}$ no additional cooling is required.

Furthermore, the subsytem comprises a driver 42a for controlling the switching transistors T. The driver 42a is controlled with the PWM signals FPGA__PWM which are generated by the associated FPGA 52a and which have a voltage level of 3V. The driver 42a transforms these signals into 12V signals and triggers thereby the upper and the lower switching transistors T (in accordance with the illustration). The driver 42a furthermore comprises a protective circuit which prevents a lower and an upper FET from being closed at the same time. The driver 42a can be deactivated through a signal FPGA__DIS from the FPGA 52a via a circuit 417. In the event of a fault the FETs can be opened within approximately 100 nanoseconds.

The current measurement device 411 for determining the phase current comprises a shunt resistor 412 of for example 10–50 milliohms and an operational amplifier 413, which amplifies the output signal of the shunt resistor 412 and transmits it to the DSP board 50a as the Current__Meas signal. The shunt resistor 412 is arranged in the H bridge between the source of a FET and the negative operating potential, here the ground potential of the 12V d. c. voltage, and delivers a signal of which the magnitude depends linearly on the phase current.

Each subsytem of the power component 4a comprises in addition an excess current safety device 414 with a further shunt resistor 415 and a further operational amplifier 416. The output of this operational amplifier 416 is connected to the circuit 417, which can switch off the driver 42a. The shunt resistor 415 of the excess current safety device 414 is arranged between the H bridge of the power amplifier 41 and the negative operating potential, here the ground potential of the 12V d. c. voltage. The voltage drop across the shunt resistor 415 is amplified in the operational amplifier and is compared with a predeterminable threshold value, from which a digital output signal Overcurrent is generated. In the event of an impermissibly high phase current (excess current) the signal FPGA_OC is sent to the associated FPGA 52*a*, which switches off the driver 42*a*. The excess current safety device 414 is designed in such a manner that it is fast enough in order to prevent a complete d. c. short circuit between the two operating potentials of the 12V d. c. voltage via the H bridge.

Each control system 5*a*, 5*b* has its own, separate and complete two-axis measurement system 80*a*, 80*b* with the position sensors 81, 82 and 83, 84 respectively for determining the radial position of the rotor 3. FIG. 16 shows the block circuit diagram of a two-axis measurement system 80*a* of this kind with the two position sensors 81 and 82, which preferably comprise in each case the two sensor elements 811, 812 and 821, 822 respectively in a 180° arrangement (see above, in particular FIG. 2 and FIG. 7). Two current position coordinates of the rotor with respect to the X-Y plane of the stator system, which will be simply designated in the following as the x and y component, can in each case be determined with each two-axis measurement system 80*a*, 80*b*. Each two-axis measurement system 80*a*, 80*b*, of which the axes are designated as the x and the y axis, comprises in addition to the sensor elements an excitation circuit 85*a*, 85*b*, a monoflop 86*a*, 86*b*, two mixers 87*a*, 87*b*, namely one for each axis, and two amplifiers 88*a*, 88*b*.

The excitation circuit 85*a* is fed with the 312 kHz frequency which is generated by the FPGA 52*a* (see FIG. 13). This signal is amplified in the excitation circuit 85*a* and supplied to the individual sensor elements 811, 812, 821, 822, which are designed here as eddy current sensors. The output signal of the excitation circuit 85*a* is monitored by the monoflop 86*a*, which generates an error signal sens_err and transmits it to the FPGA 52*a* as soon as the excitation frequency is no longer present. For the evaluation the output signal of the sensor elements 811, 812 for the x axis is supplied to a first mixer 87*a* and the output signal of the two sensor elements 821, 822 for the y axis to a second mixer 87*a*. The mixers 87*a*, for example of the type PMB2331 from the Siemens company, convert the output signals of the sensor elements, which are a. c. signals, into d. c. signals which depend on the current radial position of the rotor 3. These d. c. signals are amplified in the amplifiers 88*a* which are in each case connected after the mixers 87*a* and then transmitted to the ADC 54*a* (FIG. 12). An all-pass filter 89*a* can optionally be inserted between the outputs of the position sensor 81 and the input of the associated mixer 87*a* and between the outputs of the position sensor 82 and the input of the associated mixer 87*a* in each case in order to compensate the phase shifts between the excitation signal and the output signal of the sensor elements.

FIG. 17 shows a block circuit diagram of the field sensor 91 or 92, with which the rotor angle is determined. Each field sensor 91, 92 comprises two magnetoresistive bridges 93*a*, for example of the type IMO LK15, which generate two signals which are phase shifted by 90°, for example a sine and a cosine signal, and which depend on the angle and the amplitude of the magnetic field. An operational amplifier 94*a* which amplifies the output signal of the respective bridge 93*a* and transmits it to the ADC 54*a* (see FIG. 13), is connected after each bridge 93*a*.

FIG. 18 shows in a block circuit diagram a supply circuit 500, which supplies the control apparatus 5 with energy. The control apparatus 5 requires two different d. c. voltages, namely 3 volts and 12 volts in the exemplary embodiment described here, with 12 volts being the positive operating potential for the power amplifiers 41. The negative operating potential both for the 3V supply and for the 12V supply is in each case the ground potential GND. The supply circuit 500 is fed with a 3V and with a 12V input line which each then fork in order to supply each of the two control systems 5*a* and 5*b*. In each of the two control systems 5*a*, 5*b* the 12V supply 12V_A or 12V_B respectively for this control system can be switched on or off by means of a switching transistor 501*a*, 501*b*, for example of the type Si6954 from the Vishay company. The switching transistor 501*a*, 501*b* is in each case triggered or switched respectively by a driver 502*a*, 502*b*. As soon as the latter receives the signal dis_12V_A or dis_12V_B respectively, it interrupts the 12V supply of the corresponding control system 5*a* and 5*b* respectively via the switching transistor 501*a* and 501*b* respectively.

In the 3V supply 3V_A and 3V_B respectively of each control system a further driver 504*a*, 504*b* is provided which switches off the 3V supply of this control system 5*a* or 5*b* when the signal dis_A or dis_B respectively is present. The signal dis_A or dis_B respectively for switching off the respective 3V supply can come only from the FPGA 52*a*, 52*b* (see FIG. 13) of the respective other control system, which means that only the FPGA 52*a* of the control system 5*a* can interrupt the 3V supply of the control system 5*b*, that is, generate the signal dis_B, and only the FPGA 52*b* of the control system 5*b* can interrupt the 3V supply of the control system 5*a* that is, generate the signal dis_A.

The on/off pin for the 12V supply is connected in each case via a pull up resistor 503*a*, 503*b* to the 3V supply of the same control system. This ensures that when the 3V supply for this control system is switched off the 12V supply for this control system automatically follows and is also switched off. On the other hand the 12V supply can however be switched off independently of the 3V supply, which means that during the deactivation of the 12V supply in one of the two control systems 5*a*, 5*b* the 3V supply of this control system is maintained.

The on/off pin for the 12V supply is furthermore connected via the associated FPGA 52*a*, 52*b* to an excess current safety device 414 (see FIG. 15).

FIG. 19 shows a flow chart of a cycle of the theoretical construction of the software, which means of the program in accordance with which the control apparatus 5 works. The two control systems 5*a*, 5*b* work in parallel, with the theoretical scheme of the software being identical for both control systems 5*a*, 5*b*. The double arrows in FIG. 19 symbolically indicate the data exchange between the two control systems 5*a* and 5*b*. In step 201 (start) the cycles for the two control systems 5*a* and 5*b* are initialized by an interrupt signal which is produced by the PWM generators 521*a*, 521*b* (FIG. 13). The start time lies in an interval in which no switching of the power amplifiers 41 takes place. In step 202 (measurement of position and field) values for the rotor position and the rotor angle are measured by means of the position and field sensors. Since no disturbances by the FETs are yet present shortly after the start of the cycle, the noise is also very low in these measurements. Step 203 (error handler) is a task which runs in the background and in which each control system 5*a*, 5*b* checks on or monitors the respective other one in that for example it is tested whether the other control system responds within a predetermined time interval. If not and if the other system can not be revived by a reset, it will be switched off completely (see also FIG. 20 and the explanations in this regard). In step 204 (validation of position and field) the values for the position of the rotor and/or the values for the rotor angle which each control system 5a, 5b has measured independently of the other control system are exchanged between the two control systems 5a, 5b. The master 5a checks the values of the slave 5b and decides with the help of error routines in the event of possible deviations which of the values are correct. Where appropriate, fault-corrected values are determined. After the correct or fault-corrected values have been determined, the latter are taken over by both control systems, so that both control systems work with identical values for the position of the rotor and the rotor angle. In step 205 (calculation of forces, torque) each control system 5a, 5b executes the regulation routines for the position and the speed of the rotor and determines the required regulatory forces and torques in order to keep the rotor 3 centered in the stator 2 and in order to maintain the rotation of the rotor 3 with the desired speed of rotation. From the thus determined forces and torques the corresponding phase currents for the individual drive and control phases are determined. In step 206 (current controller) the power amplifiers are excited in such a manner that they imprint the previously measured phase currents into the loop of the respective drive or control phase.

In the normal, which means fault-free, operating state the two control systems 5a, 5b work in parallel (hot redundancy). Each control system 5a, 5b carries out its own position and field measurement, calculates the required forces and the required torque, and accordingly supplies the control phases and the drive phase with the respective phase current. As already mentioned, the control systems 5a, 5b exchange with one another the values for the position of the rotor and for the rotor angle which were in each case determined by them in order to attune them to one another. Through this it is ensured that the two control systems 5a, 5b do not work against one another.

If now a fault arises in one of the two control systems 5a or 5b, then different fault modes are provided in which the bearingless motor 1 can be operated without the correct magnetic journalling or the correct driving of the rotor being endangered. In the following, several fault modes will now be explained, with reference being made in an exemplary manner to the control system 5a. It is self evident that in each case a corresponding fault mode is also present for the case that the same fault arises in the control system 5b. The letter A in the designation of the fault mode indicates that reference is being made to control system 5a.

The fault mode 1 (A) arises when a fault is present in the two-axis measurement system 80a with the position sensors 81, 82. Then this measurement system is completely switched off and only the position values which are measured by the control system 5b are used for both control systems 5a, 5b.

The fault modes 1(Ax) and (1Ay) arise when only one axis, namely the x or the y axis of the two-axis measurement system 80a is faulty. Accordingly, only the one axis x or y is switched off and the position value which is measured by the still fault-free axis continues to be used for determining the position of the rotor.

The fault mode 2(A) arises when the field sensor 91 of the control system 5a is working in a faulty manner and is switched off. In this mode the measurement of the rotor angle takes place only with the field sensor 92 of the control system 5b.

The fault mode 3(A) means that the 12V supply of the control system 5a is completely switched off. In this mode all three power amplifiers 41 of the control system 5a are deactivated, and the bearingless motor 1 is operated only with the drive phase and the two control phases which are controlled by the control system 5b. The DSP 51a and the position sensors 81, 82 as well as the field sensor 91 of the control system 5a are still working in this fault mode 3(A).

For the case that a fault arises only in one or in two power amplifier(s) 41 of the control system 5a or in one or two of the drive and control phases which are controlled by the control system 5a, only the respective faulty electrical phase is switched off. A fault of this kind can for example be a line breakage or a short circuit in one of the drive or control coils. For these cases the six fault modes 3(A1), 3(A2), 3(A3), 3(A1,2), 3(A1,3), 3(A1,3) are provided, with the number or the numbers in the parentheses indicating in each case which of the phases is switched off in the respective fault mode. In this the number 1 indicates the drive phase and the numbers 2 and 3 the control phases. Thus for example the fault mode 3(A1,3) means that the drive phase (1) and one of the two control phases (3) is switched off and the other control phase (2) is still being operated.

In fault mode 4(A) the entire control system 5a is switched off. The bearingless motor 1 is operated only with the control system 5b and the three phases which are controlled by this control system 5b.

FIGS. 20a, 20b and 20c show in their entirety a flow chart which illustrates a possible run-through of a fault detection routine, such as is carried out in step 203 of the software cycle (see FIG. 19). The sequence of the individual checks is however to be understood only in an exemplary manner. Reference is again made to the control system 5a. The routine for the control system 5b has an analogous appearance.

Starting from the normal operating state 100 (FIG. 20a) the inter-processor connections 58, 59 are checked in step 101. If the control system 5b does not respond, then the watchdog 57b of the control system 5b is sampled in step 102. If the latter is at zero, the 3V supply of the control system 5b is switched off in step 103 and the fault mode 4(B) is chosen in step 103'. If the watchdog 57b is not at zero or if the inter-processor connection is in order, then excessive current is tested for in steps 104 to 106. If an excessive current flows in the 3V supply (step 104; overcurrent 3V?), the 3V supply is switched off in step 104' and the fault mode 4(A) is chosen in step 104". If an excessive current flows in the 12V supply (step 105; oc 12V?), all three power amplifiers 41 are switched off in step 105', and the fault mode 3(A) is chosen in step 105". If an excessive current (oc) flows in one of the three phases ch_x, ch_y,ch_d (step 106), the corresponding power amplifier 41 (H bridge) is switched off in step 106' and the associated fault mode is chosen in step 106". In step 107 the individual phase currents are checked for plausibility (check current of ch_d, ch_x and ch_y). If this test turns out negatively for one of the three phases, the routine continues with step 106' (see above). In step 108 (FIG. 20b) it is tested whether a fault signal sens_err from the two-axis measurement system 80a, 80b is present. If so, a change is made in step 108' to the fault mode 1 (A); if not, it is tested in step 109 whether the values of the position sensors exceed a predetermined range (pos_sens_check; limits exceed range?). If so, a change into the fault mode 1 (Ax) or 1 (Ay) is made in step 109'. In step 110 the field sensor 91 is checked (field_sens_check). If the root mean square (RMS) value lies outside a predetermined range (step 110', field_RMS out of range?) or is equal to zero (step 110", field_RMS=0?) the fault mode 2(A) is chosen in step 110'''. In step 110'''' it is tested for both components of the signal of the field sensor whether its average value is different from zero (field x or y average not 0?). If so, a calibration (on-line alignment) of the field sensors 91 is carried out in step 111. In step 112 the FPGA 52a is tested (FPGA_test). If faults are detected in this process, then a change into the fault mode 3(A) is made in step 112'. In step 113 (FIG. 20c) the flash memory 53a is tested (flash_test). If the latter does not respond or if it can not be revived, then it is registered in step 114 that the control system 5a can not be started anew, but that the normal operating state can be maintained. In step 115 the ADCs 54a are tested (ADC_test). If faults are detected in this test, it is checked in step 116 which of the two ADCs 54a is faulty and a change into the fault mode 3(A1,2) or 3(A1,3) is made accordingly in step 116' or 116". In step 117, finally, the software is tested (software deadlock). If individual software modules take longer than they should (e.g. in a hang-up of the software), the watchdog is no longer addressed, which leads to a reset. The other control system 5b monitors the reset and switches the control system 5a off after a repeated occurrence of the fault. If a fault arises in this test, all power amplifiers (H bridges) of the control system 5a are switched off in step 118, and a change into the fault mode 4(A) is made in step 118' in that the other control system 5b deactivates the entire control system 5a. If all tests have led to a positive, that is, a fault-free, result, the normal operating state is continued (step 119).

Through the various fault modes it is possible to react very flexibly to a large number of different types of faults in an ideally adapted manner. In the following it will be indicated in a non exclusive listing and in tabular form how different faults are detected and eliminated. In this, reference will again be made only to the control system 5a. Naturally the explanations hold in an analogous manner for the other control system 5b as well. In the first column of the table an index number is in each case specified; in the second column the fault is specified, in the third column it is indicated how or with which elements the fault can be detected; and in the fourth column it is indicated how the fault is reacted to and where appropriate the fault mode which is used. Fault mode will be abbreviated in this with FM. The abbreviation IPV stands for inter-processor connection.

| | | | |
|---|---|---|---|
| 1 | Two axis measurement system 80a | | |
| 1.1 | No excitation | | |
| 1.1.1 | No clock pulse from DSP 51a | DSP dead; no IPV; Watchdog | Switch off control system 5a; FM 4(A) |
| 1.1.2 | No clock pulse from FPGA 52a | FPGA dead; DSP of the control system 5b | See 1.1.1 |
| 1.1.3 | Cable breakage | Sens_err signal monoflop 86a | Switch off measurement system; FM 1(A) |
| 1.1.4 | Damage in the excitation circuit 85a | See 1.1.3 | See 1.1.3 |
| 1.2 | Position sensor 81, 82/Mixer 87a | | |
| 1.2.1 | Dropout of the mixer 87a | Sensor test in DSP | Switch off the axis FM 1(Ax) or 1(Ay) |
| 1.2.2 | Dropout of amplifier 88a | Sensor test in DSP | See 1.2.1 |
| 1.2.3 | Dropout of the sensor (short circuit) | Sens_err signal monoflop 86a | See 1.1.3 |
| 1.2.4 | Dropout of the sensor (open) | Sensor test in DSP | See 1.2.1 |
| 1.3 | Amplification/Offset | | |
| 1.3.1 | Aging resistors | Sensor test in DSP | See 1.2.1 |
| 1.3.2 | Temperature effects | Sensor test in DSP | See 1.2.1 |
| 1.4 | Cable breakage | | |
| 1.4.1 | All cables | Sens_err signal goes high | See 1.2.1 |
| 1.4.2 | One cable | Sensor test in DSP | See 1.2.1 |
| 1.5 | Drift of the excitation frequency | | |
| 1.5.1 | Aging condensers | Sensor test in DSP | See 1.2.1 |
| 1.5.2 | Temperature effects | Sensor test in DSP | See 1.2.1 |
| 2 | Field sensor 91 | | |
| 2.1 | No excitation | | |
| 2.1.1 | No 3 V supply (Cable breakage) | Signal at limit | Switch off field sensor; FM 2(A) |
| 2.1.2 | Neither 3 V nor GND (Cable breakages) | Signal floating; RMS of the signal not correct | See 2.1.1 |
| 2.2 | Break in sensor chip | | |
| 2.2.1 | Short circuit of internal resistors | Signal at limit | See 2.1.1 |
| 2.2.2 | Internal resistors open (do not conduct) | Signal floating; RMS of the signal not correct | See 2.1.1 |
| 2.3 | Drift | | |
| 2.3.1 | Offset drift (aging) | Average value not zero | Calibration on-line (no fault) |
| 2.3.2 | Amplification (aging) | RMS of the Signals not correct | See 2.3.1 |
| 2.4 | Dropout of the operational amplifier 94a | | |
| 2.4.1 | Short circuit of output or resistors | Signal at limit | See 2.1.1 |
| 2.4.2 | Open output | Signal floating: RMS of the signal not correct | See 2.1.1 |
| 2.4.3 | Drift offset | See 2.3.1 | See 2.3.1 |
| 2.4.4 | Drift amplification | See 2.3.1 | See 2.3.1 |
| 2.5 | Cable breakages | | |
| 2.5.1 | All cables | See 2.1.2 | See 2.1.2 |
| 2.5.1 | Individual cables | Signal at limit, constant or floating | See 2.1.1 |

-continued

| | | | |
|---|---|---|---|
| 3 | Drive | | |
| 3.1 | Loop of the drive winding | | |
| 3.1.1 | Total short circuit | Excessive current (no load) | Switch off associated H bridge, FM 3(A1) |
| 3.1.2 | Partial short circuit Inductance still large | No fault | None |
| 3.1.3 | Partial short circuit Inductance low | See 3.1.1 | See 3.1.1 |
| 3.1.4 | Loop not conducting | No current | Switch off power component 4a, FM 3(A) |
| 3.2 | Supply | | |
| 3.2.1 | Short circuit to GND | Excessive current 12 V supply | See 3.1.4 |
| 3.2.2 | Short circuit to 12 V | See 3.2.1 | See 3.2.1 |
| 4 | Journalling | | |
| 4.1 | Loops of the control winding | | |
| 4.1.1 | Total short circuit | Excessive current (no load) | Switch off associated H bridge, FM 3(A1) |
| 4.1.2 | Partial short circuit Inductance still large | No fault | None |
| 4.1.3 | Partial short circuit Inductance low | See 4.1.1 | See 4.1.1 |
| 4.1.4 | Loops not conducting | No current | See 4.1.1 |
| 4.2 | Supply | | |
| 4.2.1 | Short circuit to GND | Excessive current 12 V supply | Switch off power component 4a, FM 3(A) |
| 4.2.2 | Short circuit to 12 V | See 4.2.1 | See 4.2.1 |
| 5 | Power component 4a | | |
| 5.1 | Excessive current | | |
| 5.1.1 | Short circuit of a FET | Excess current safety device 414 (Hardware) | Switch off associated H bridge, FM 3(A1), 3(A2) or 3(A3) |
| 5.1.2 | Short circuit of loop | See 5.1.1 | See 5.1.1 |
| 5.1.3 | Dropout of the driver 42a | See 5.1.1 | See 5.1.1 |
| 5.1.4 | Dropout of the excess current safety device | See 5.1.1 | See 5.1.1 |
| 5.1.5 | PWM signal blocked | Excessive current detection (Software) | Switch off power component 4a (12 V supply) FM 3(A) |
| 5.2 | No current | | |
| 5.2.1 | PWM signal blocked | Sum of the RMS is zero, whereas voltage is not equal to zero | Switch off associated H bridge FM 3(A1), 3(A2) or 3(A3) |
| 5.2.2 | FET open (not conducting) | See 5.2.1 | See 5.2.1 |
| 5.2.3 | Dropout of the current measurement device. | See 5.2.1 | See 5.2.1 |
| 5.2.4 | Dropout of the driver 42a FET | See 5.2.1 | See 5.2.1 |
| 5.3 | Condenser in the d. c. connection | | |
| 5.3.1 | Short circuit of condenser | Excessive current 12 V input | Switch off 12 V; FM 3(A) |
| 5.3.2 | Condenser open | No fault | None |
| 6 | DSP board 50a | | |
| 6.1 | DSP 51a | | |
| 6.1.1 | Dropout of the DSP | No IPV, watchdog 57a | Switch off control system 5a FM 4(A) |
| 6.1.2 | No 3 V supply | No IPV, watchdog 57a | See 6.1.1 |
| 6.1.3 | No 1.8 V supply | No IPV, watchdog 57a | See 6.1.1 |
| 6.1.4 | Software deadlock | Watchdog 57a, FPGA watchdog | Switch off power component 4a and 12 V immediately; as in 6.1.1 |
| 6.2 | Inter-processor communication | | |
| 6.2.1 | Dropout of the FPGA 52a | No IPV | See 6.1.1 |
| 6.2.2 | Dropout of the driver 58l, 59la | No IPV | See 6.1.1 |
| 6.3 | ADC 54a | | |
| 6.3.1 | Dropout of the ADC, impossible values | ADC test negative | Switch off corresponding phases FM 3(A1,2) or 3A(1,3) |
| 6.3.2 | Dropout of the ADC, impossible values | See 6.3.1 | See 6.3.1 |
| 6.4 | FPGA 52a | | |
| 6.4.1 | No clock pulse from DSP | Dropout of the DSP: FPGA_watchdog (clocked by control system 5b) | Switch off power component 4a, FM 4(A) |
| | | Dropout of the clock output: FPGA_test does not count | Switch off power component 4a, FM 4(A) |
| 6.4.2 | No 3 V supply | See 6.1.1 | See 6.1.1 |
| 6.4.3 | PWM outputs blocked | Excessive current or no current (software) | Switch off power component 4a, FM 4(A) |

| | | | |
|---|---|---|---|
| 6.4.4 | Outputs power_enable blocked | Operation still possible | None |
| 6.5 | Flash memory 53a | | |
| 6.5.1 | Dropout of the flash memory | No new start, check sum incorrect | No action during operation |
| 6.5.2 | Dropout of the flash burning function | | No action during operation |
| 6.6 | Periphery | | |
| 6.6.1 | No clock signal | DSP not working, no IPV | Switch off control system 5a, FM 4(A) |
| 6.6.2 | Dropout of the watchdog 57a | Reset DSP during normal operation | Switch off control system 5a, FM 4(A) |
| 6.6.3 | Linear regulator 56a (1.8 V) | See 6.1.3 | See 6.1.3 |
| 7 | Supply circuit 500 | | |
| 7.1 | 3 V supply | | |
| 7.1.1 | Short circuit in the 3 V system | Excessive current 3 V supply | Switch off control system 5a (3 V and 12 V); FM 4(A) |
| 7.1.2 | Open 3 V switch 504a | No IPV, watchdog 57a | Other control system takes over; FM 4(A) |
| 7.2 | 12 V supply | | |
| 7.2.1 | Short circuit in the 12 V system | Excessive current 12 V supply | Switch off 12 V supply FM 3(A) |
| 7.2.2 | 12 V supply open (interruption) | No current in the H bridges | Other power component 4b takes over, measurement systems still working; FM 3(A) |

In the table "signal at limit" means that the associated signal takes on its maximum or minimum possible value. The "sensor test in DSP" comprises for example the test carried out in step 109 (see FIG. 20) in which it is tested whether the values of the position sensors lie within predetermined limits. The sensor test can however also comprise other measures: Since each of the two position sensors 81, 82 of the control system 5*a* comprises two sensor elements 811, 812 and 821, 822 respectively in a 180° arrangement (see above), systematic faults (offsets, temperature effects, aging effects) can be detected and compensated (calibration) through the taking of differences. It is also possible to test the signals of the individual position sensors or sensor elements respectively for mutual compatibility in that for example from each pair of signals a third is calculated and compared with the corresponding measured signal (two out of three test). In this way a faulty sensor element can be identified. Furthermore, it is possible for the detection of faults to compare with one another the position values which were measured independently of one another by the two control systems 5*a* and 5*b*. Since a total of four is independent position values for the two coordinates of the rotor 3 in the X-Y plane are present from the two control systems 5*a*, 5*b*, it can be determined on the basis of this overdetermined system of equations (four equations, two unknowns), whether one of the position values is false and if so, which one. The same also holds for the values of the two independent field sensors. These also form a system of equations with four equations and two unknowns.

Through the invention a blood pump is furthermore proposed which comprises a rotary drive in accordance with the invention, and which is also suitable in particular for implantation into a body. FIG. 21 shows in a highly schematized illustration a cross-section through a preferred exemplary embodiment of a blood pump in accordance with the invention which is designated in its entirety by the reference symbol 10 and which is designed as a centrifugal pump.

The rotary drive in accordance with the invention with the stator 2 and the rotor 3 is preferably designed as a temple motor (see also FIG. 9) with eight in each case L-shaped stator teeth, of which only two can be seen in FIG. 21, namely those designated by 21 and 25. The stator teeth 21, 25 are magnetically coupled to one another via the ring-shaped iron yoke 20. The discrete drive coils 611, 621 and the discrete control coils 711, 721, 731, 741 of the drive winding and of the control winding respectively are arranged around the long limb of the stator teeth 21, 25, as has been described above. In this, four concentrated drive coils 611, 621 are provided as shown in FIG. 2 and are connected together to form the two loops 61, 62 of the drive winding as illustrated in FIG. 5. In the exemplary embodiment in accordance with FIG. 21 either eight concentrated control coils 711, 712, 731, 741 are provided, namely one on each stator tooth, analogously as is shown in FIG. 2, or sixteen concentrated control coils 711, 712, 713, 714, namely two on each stator tooth, analogously as is shown in FIG. 7. In the latter case the two control coils which are provided on the same stator tooth are preferably wound in each case one on the other, as was explained above. The eight or sixteen control coils respectively are connected together in a manner which is analogous to that illustrated in FIG. 4 or in FIG. 8 respectively to form the four loops 71–74 of the control winding. The rotary drive of the blood pump 10 thus has two drive phases and four control phases in this exemplary embodiment.

The permanent-magnetically excited rotor 3 with the permanent-magnetic ring 31 and the iron yoke 32 furthermore has a jacketing 33, preferably of plastic, and a plurality of vanes 34 for the forwarding of the blood, which means that the rotor 3 of the rotary drive also serves as a pump rotor. It thus forms a so-called integral rotor. The rotor 3 is magnetically journalled in the stator 2 during operation and is driven by the stator 2, so that it rotates about the axis of rotation A.

The rotor 3 is arranged in a pump housing 11 which has an inlet 12 for the blood to be forwarded. During operation the blood, symbolically indicated by the arrows without reference symbols, flows through the inlet 12 and then out of the axial direction in the direction towards the rotor 3, where it is deflected by the vanes 34 into the radial direction and is forwarded into an outlet passage 13, which discharges into an outlet which can not be recognized in FIG. 21. As the arrows indicate, a portion of the blood flows in the axial direction completely through the rotor 3, so that it causes a hydrodynamic journalling beneath the rotor 3 in the illustration, which supports the magnetic journalling.

The operation of the blood pump 10 is particularly preferably regulated and controlled with the control apparatus 5 which was described above in detail and which comprises the two separate control systems 5a, 5b. In regard to a design which is as compact as possible the control systems 5a, 5b are in each case realized in the form of a plurality of electronic prints or chips, which are arranged at least partly in the interior of the rotary drive. As FIG. 21 shows, those electronic prints which carry the power components 4a, 4b with the power amplifiers 41 are preferably arranged in the interior of the rotary drive in the space surrounded by the stator teeth 21, 25 and below the rotor in the illustration. In addition to the advantage of an ideal exploitation of the available space and thus of a very compact construction, this measure has the advantage that the individual power amplifiers 41 can be connected in each case directly, that is, without cables, to the associated drive and control coils respectively. Through this measure the number of cables or cable wires respectively which must be led away from the rotary drive to the outside is as low as possible. This represents a considerable increase in the operating reliability, because experience shows cable connections to have the highest dropout rate. Through the low number of the cable connections it is possible in addition to design all cable connections redundantly in order to realize a fault tolerance here as well.

The DSP boards 50a, 50b are preferably arranged directly below the stator 2 as illustrated.

A further advantageous measure consists in providing an evaluation module 8 for the position sensors 81, 82 and 83, 84 respectively which is designed as a ring-shaped electronic print and which is arranged in such a manner on the shorter limbs of the stator teeth 21, 25 that the components which are provided on the electronic print, in particular the position sensors, are located in the free space between the stator teeth 21, 25. As FIG. 21 shows, the evaluation module 8 is arranged between the short limbs of the stator teeth 21, 25 and the pump housing 11. The evaluation module 8 is for example constructed or equipped respectively as shown in FIG. 16 and preferably comprises both two-axis measurement systems 80a, 80b.

A further advantageous measure consists in connecting the individual electronic prints to one another through flexprints. The solid, that is, the substantially rigid, electronic prints then form a so-called rigid flex compound together with the flexible connection prints, which can be manufactured, equipped and tested as a unit.

The blood pump 10 is distinguished by its extremely high operating reliability, its fault tolerance, with which it can react to a large number of faults of different nature without the correct operation both with respect to the driving of the rotor 3 and to its magnetic journalling thereby being endangered, its very compact, space saving design, the optimized use of the available space and the comparatively low energy requirement, while having a high performance at the same time.

What is claimed is:

1. An electrical rotary drive, designed as a bearingless motor comprising:
    a magnetically journalled rotor;
    a stator comprising:
        a drive winding comprising at least two loops for producing a magnetic drive field which produces a torque on the rotor; and
        a control winding comprising at least three loops for producing a magnetic control field to regulate the position of the rotor with respect to the stator;
    wherein each loop of the drive winding belongs to a different electrical drive phase and each loop of the control winding belongs to a different electrical control phase; and
    a setting device that supplies each loop of the drive winding and each loop of the control winding with a phase current or a phase voltage as a setting parameter;
    wherein the setting device is designed in such a manner that the setting parameter for each loop of the drive winding and for each loop of the control winding can be regulated independently of the setting parameters for the other loops; and
    wherein the drive winding has a number of pole pairs equal to p and the control winding has a number of pole pairs equal to p±1.

2. The rotary drive in accordance with claim 1, wherein the setting device for each loop of the drive winding and for each loop of the control winding comprises a separate bipolar power amplifier which is integrated into a control apparatus for the rotary drive.

3. The rotary drive in accordance with claim 1, wherein the stator has a plurality of stator teeth connected by a yoke, said teeth being L shaped, and each tooth having a longer limb extending in an axial direction, defined by the desired axis of rotation of the rotor, and a shorter limb extending radially inward.

4. The rotary drive in accordance with claim 3, wherein an evaluation module provided for position sensors is designed as an electronic print and arranged on the shorter limb of each stator tooth so that a plurality of components provided on the electronic print is located in a free space between the stator teeth.

5. The rotary drive in accordance with claim 1, wherein the rotary drive comprises three drive phases and three control phases.

6. The rotary drive in accordance with claim 1, wherein the rotary drive comprises two drive phases and four control phases.

7. The rotary drive in accordance with claim 1, wherein the stator has eight stator teeth.

8. The rotary drive in accordance with claim 7, wherein the rotary drive comprises two drive phases, the drive winding comprises four drive coils, and each drive coil is wound around two adjacent stator teeth, and wherein each pair of two diametrically opposite drive coils forms a loop of the drive winding and belongs to the same drive phase.

9. The rotary drive in accordance with claim 1, wherein the control winding comprises a plurality of control coils and each control coil is wound around a different stator tooth.

10. The rotary drive in accordance with claim 1, wherein the control winding comprises a plurality of control coils and wherein a control coil wound around a first stator tooth and a control coil wound around a stator tooth adjacent to the tooth adjacent to the first stator tooth define a control loop and belong to the same control phase.

11. The rotary drive in accordance with claim 10, wherein the control winding comprises four control loops corresponding to four control phases.

12. The rotary drive in accordance with claim 1,
    wherein the control winding comprises four control loops having four control coils, said control loops corresponding to four control phases,
    wherein the control coils of two of the control loops are wound around a first stator tooth, a third stator tooth, a fifth stator tooth and a seventh stator tooth, wherein the control coils of the two remaining control loops are wound around a second stator tooth, a fourth stator tooth, a sixth stator tooth and an eighth stator tooth, and wherein the first through eighth stator teeth are adjacent and ordered sequentially.

13. The rotary drive in accordance with claim 12, wherein the two control coils wound around the same stator tooth are concentric, such that an outer control coil surrounds an inner control coil.

14. The rotary drive in accordance with claim 1, further comprising two separate control systems, each control system comprising:

at least two position sensors for measuring the radial position of the rotor in the stator;

means for determining the rotor angle;

at least three power amplifiers for supplying the individual loops of the drive winding and the individual loops of the control winding; and a signal processing and regulation device for regulating the drive and the position of the rotor and for controlling the power amplifiers;

wherein each control system controls at least one drive phase and at least two control phases.

15. The rotary drive in accordance with claim 14, further comprising communication means for communicating between the two control systems.

16. The rotary drive in accordance with claim 15, wherein the two control systems are configured to:

exchange, via the communication means:
values for the position of the rotor, determined by the position sensors; and
values for the rotor angle, determined by the means for determining the rotor angle;

check values for errors for at least one of the rotor's position and the rotor angle;

determine fault-corrected values; and use the determined fault-corrected values for at least one of regulating the radial position of the rotor and for regulating the drive.

17. The rotary drive in accordance with claim 1, further comprising an energy supply and fault detection means for determining faults in at least one of the following:

control systems;

individual drive phases;

individual control phases; and energy supply.

18. The rotary drive in accordance with claim 17, wherein in the event of detection of a fault, the fault detection means eliminate the fault or switch over the rotary drive into a suitable fault mode.

19. The rotary drive in accordance with claim 1, wherein each control system is designed at least partly in a form of electronic prints arranged in the interior of the rotary drive.

20. The rotary drive in accordance with claim 19, wherein the electronic prints comprise a plurality of power amplifiers, each power amplifier being coupled to associated drive coils and control coils.

21. A blood pump comprising an electrical rotary drive, the rotary drive comprising:

a magnetically journalled rotor;

a stator comprising:
a drive winding comprising at least two loops for producing a magnetic drive field which produces a torque on the rotor; and
a control winding comprising at least three loops for producing a magnetic control field to regulate the position of the rotor with respect to the stator;
wherein each loop of the drive winding belongs to a different electrical drive phase and each loop of the control winding belongs to a different electrical control phase; and a setting device that supplies each loop of the drive winding and each loop of the control winding with a phase current or a phase voltage as a setting parameter;

wherein the setting device is designed in such a manner that the setting parameter for each loop of the drive winding and for each loop of the control winding can be regulated independently of the setting parameters for the other loops;

wherein the drive winding has a number of pole pairs equal to p and the control winding has a number of pole pairs equal to p±1; and wherein the rotor of the rotary drive is permanent-magnetically excited and has a plurality of vanes for forwarding blood, so that the rotor of the rotary drive also serves as pump rotor.

* * * * *